(12) United States Patent
Liang et al.

(10) Patent No.: US 7,803,951 B2
(45) Date of Patent: Sep. 28, 2010

(54) GLUCAGON RECEPTOR ANTAGONIST COMPOUNDS, COMPOSITIONS CONTAINING SUCH COMPOUNDS AND METHODS OF USE

(75) Inventors: Rui Liang, East Brunswick, NJ (US); Emma R. Parmee, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 564 days.

(21) Appl. No.: 11/887,125

(22) PCT Filed: Mar. 24, 2006

(86) PCT No.: PCT/US2006/010551

§ 371 (c)(1), (2), (4) Date: Sep. 24, 2007

(87) PCT Pub. No.: WO2006/104826

PCT Pub. Date: Oct. 5, 2006

(65) Prior Publication Data

US 2009/0054506 A1    Feb. 26, 2009

Related U.S. Application Data

(60) Provisional application No. 60/666,488, filed on Mar. 30, 2005.

(51) Int. Cl.
C07D 257/00 (2006.01)
A61K 31/41 (2006.01)

(52) U.S. Cl. .......... 548/251; 549/365; 549/440; 562/455; 514/381; 514/456; 514/464; 514/538

(58) Field of Classification Search .......... 514/381, 514/456, 464, 538; 548/251; 549/365, 440; 562/455

See application file for complete search history.

(56) References Cited

U.S. PATENT DOCUMENTS

| 5,776,954 A | 7/1998 | de Laszlo et al. |
| 6,503,949 B1 | 1/2003 | Lau et al. |
| 6,765,009 B2 | 7/2004 | Francesco et al. |
| 2003/0158226 A1 | 8/2003 | Belloni et al. |

FOREIGN PATENT DOCUMENTS

| EP | 1 489 077 | 12/2004 |
| WO | WO 9415917 | * 7/1994 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 99/01423 | 1/1999 |
| WO | WO 99/32448 | 7/1999 |
| WO | WO 00/39088 | 7/2000 |
| WO | WO 00/69810 | 11/2000 |
| WO | WO 02/00612 | 1/2002 |
| WO | WO 02/40444 | 5/2002 |
| WO | WO 03/048109 | 6/2003 |
| WO | WO 03/051357 | 6/2003 |
| WO | WO 03/053938 | 7/2003 |
| WO | WO 03/064404 | 8/2003 |
| WO | WO 03/097619 | 11/2003 |
| WO | WO 2004/002480 | 1/2004 |

OTHER PUBLICATIONS

R. Kurukulasuriya et al., "Biaryl amide glucagon receptor antagonists", Bioorganic & Medicinal Chemistry Letters, vol. 14, pp. 2047-2050 (2004).

* cited by examiner

Primary Examiner—Shailendra Kumar
(74) Attorney, Agent, or Firm—Richard C. Billups; John C. Todaro

(57) ABSTRACT

Substituted aryl and heteroaryl derivatives are disclosed. The compounds are useful for treating type 2 diabetes and related conditions. Pharmaceutical compositions and methods of treatment are also included.

19 Claims, No Drawings

GLUCAGON RECEPTOR ANTAGONIST COMPOUNDS, COMPOSITIONS CONTAINING SUCH COMPOUNDS AND METHODS OF USE

CROSS-REFERENCE TO RELATED APPLICATIONS

This application is a U.S. National Phase application under 35 U.S.C. §371 of PCT Application No. PCT/US2006/010551, filed Mar. 24, 2006, which claims priority under 35 U.S.C. §119 from U.S. provisional application No. 60/666,488, filed Mar. 30, 2005.

BACKGROUND OF THE INVENTION

The present invention relates to substituted aryl and heteroaryl derivatives, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level >126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure >130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by alpha cells in pancreatic islets in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of glucagon are useful in improving insulin responsiveness in the liver, decreasing the rate of glycogenolysis and gluconeogenesis and lowering the rate of hepatic glucose output resulting in a decrease in the levels of plasma glucose.

SUMMARY OF THE INVENTION

The present invention is directed to a compound represented by formula I:

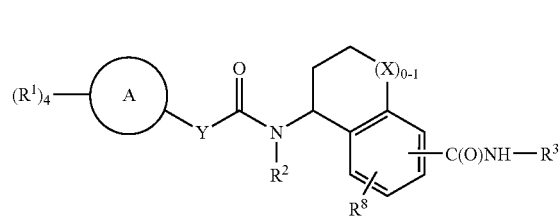

or a pharmaceutically acceptable salt or solvate thereof, wherein:

ring A is selected from the group consisting of: 6-10 membered aryl and 5-10 membered heteroaryl, said heteroaryl containing from 1-4 heteroatoms, 0-2 of which are O or S atoms, and 0-4 of which are N;

Y is present or absent, and when present, represents O, S, NH or $CH_2$;

X is present or absent, and when present, represents O or $CH_2$;

each $R^1$ is H or is selected from the group consisting of:
(a) halo, OH, $CO_2R^4$, $SO_pR^5$, CN, $NO_2C(O)NR^6R^7$ or $NR^6R^7$;
(b) $C_{1-10}$alkyl, $C(O)C_{1-6}$alkyl or $OC_{1-6}$alkyl, the alkyl portions being optionally substituted with: (1) 1-5 halo groups, up to perhalo, and 1-2 groups selected from OH, $CO_2R^4$, $SO_pR^5$, CN, $NO_2C(O)NR^6R^7$, $NR^6R^7$ and phenyl optionally substituted with 1-3 halo groups and 1-2 groups selected from: OH, $C_{1-3}$alkyl, halo$C_{1-3}$alkyl, CN, $OC_{1-3}$alkyl and Ohalo$C_{1-3}$alkyl;
(c) a 6-10 membered aryl or aryloxy group, said groups being optionally substituted with 1-3 halo groups and 1-2 groups selected from: OH, $C_{1-3}$alkyl, halo$C_{1-3}$alkyl, CN, $OC_{1-3}$alkyl and Ohalo$C_{1-3}$alkyl;

$R^2$ is $C_{1-10}$alkyl or aryl optionally substituted with 1-3 groups selected from (a), (b) and (c) above;

$R^3$ represents $CH_2CH_2CO_2R^4$, $CH_2CH(OH)CO_2R^4$, $CH_2CF_2CO_2R^4$ or 5-tetrazolyl;

$R^4$ is H or $C_{1-6}$alkyl, and $R^5$ represents a member selected from the group consisting of: $C_{1-10}$alkyl, Aryl or Ar—$C_{1-10}$alkyl, said $C_{1-10}$alkyl, Aryl and Ar—$C_{1-10}$alkyl being optionally substituted with 1-3 halo groups;

$R^6$ and $R^7$ each independently represent H or $C_{1-3}$alkyl, $R^8$ is selected from the group consisting of: H, OH, $C_{1-3}$alkyl, halo$C_{1-3}$alkyl, CN, $OC_{1-3}$alkyl and Ohalo$C_{1-3}$alkyl, and p is 0, 1 or 2.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and teat-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, unless otherwise specified, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2, 3-b)pyridyl, benzoxazinyl, tetrahydrohydroquinolinyl, tetrahydroisoquinolinyl, dihydroindolyl, and the like The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

In one aspect, the invention is directed to a compound represented by formula I:

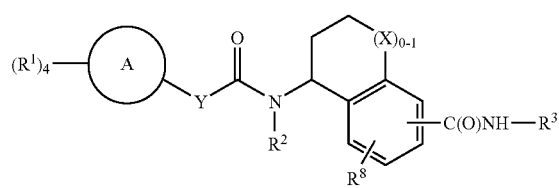

I or a pharmaceutically acceptable salt or solvate thereof, wherein:

ring A is selected from the group consisting of: 6-10 membered aryl and 5-10 membered heteroaryl, said heteroaryl containing from 1-4 heteroatoms, 0-2 of which are O or S atoms, and 0-4 of which are N;

Y is present or absent, and when present, represents O, S, NH or $CH_2$;

X is present or absent, and when present, represents O or $CH_2$;

each $R^1$ is H or is selected from the group consisting of:

(a) halo, OH, $CO_2R^4$, $SO_pR^5$, CN, $NO_2C(O)NR^6R^7$ or $NR^6R^7$;

(b) $C_{1-10}$alkyl, $C(O)C_{1-6}$alkyl or $OC_{1-6}$alkyl, the alkyl portions being optionally substituted with: (1) 1-5 halo groups, up to perhalo, and 1-2 groups selected from OH, $CO_2R^4$, $SO_pR^5$, CN, $NO_2C(O)NR^6R^7$, $NR^6R^7$ and phenyl optionally substituted with 1-3 halo groups and 1-2 groups selected from: OH, $C_{1-3}$alkyl, halo$C_{1-3}$alkyl, CN, $OC_{1-3}$alkyl and Ohalo$C_{1-3}$alkyl;

(c) a 6-10 membered aryl or aryloxy group, said groups being optionally substituted with 1-3 halo groups and 1-2 groups selected from: OH, $C_{1-3}$alkyl, halo$C_{1-3}$alkyl, CN, $OC_{1-3}$alkyl and Ohalo$C_{1-3}$alkyl;

$R^2$ is $C_{1-10}$alkyl or aryl optionally substituted with 1-3 groups selected from (a), (b) and (c) above;

$R^3$ represents $CH_2CH_2CO_2R^4$, $CH_2CH(OH)CO_2R^4$, $CH_2CF_2CO_2R^4$ or 5-tetrazolyl;

$R^4$ is H or $C_{1-6}$alkyl, and $R^5$ represents a member selected from the group consisting of: $C_{1-10}$alkyl, Aryl or Ar—$C_{1-10}$alkyl, said $C_{1-10}$alkyl, Aryl and Ar—$C_{1-10}$alkyl being optionally substituted with 1-3 halo groups;

$R^6$ and $R^7$ each independently represent H or $C_{1-3}$alkyl, $R^8$ is selected from the group consisting of: H, OH, $C_{1-3}$alkyl, halo$C_{1-3}$alkyl, CN, $OC_{1-3}$alkyl and Ohalo$C_{1-3}$alkyl, and p is 0, 1 or 2.

Another aspect of the invention that is of interest relates to a compound of formula I or a pharmaceutically acceptable salt or solvate thereof wherein ring A is selected from the group consisting of: phenyl, naphthyl, indole, 4H-1,3-benzodioxine and 1,3-benzodioxole. Within this aspect of the invention, all other variables are as originally defined with respect to formula I.

Of particular interest within this subset are compounds of the invention wherein ring A represents phenyl. Within this aspect of the invention, all other variables are as originally defined with respect to formula I.

Another aspect of the invention that is of interest relates to a compound of formula I or a pharmaceutically acceptable salt or solvate thereof wherein Y is absent or is selected from the group consisting of NH and $CH_2$. Within this aspect of the invention, all other variables are as originally defined with respect to formula I.

Another aspect of the invention that is of interest relates to a compound of formula I or a pharmaceutically acceptable salt or solvate thereof wherein X is absent or represents $CH_2$. Within this aspect of the invention, all other variables are as originally defined with respect to formula I.

Another aspect of the invention that is of interest relates to a compound of formula I or a pharmaceutically acceptable salt or solvate thereof wherein X is O. Within this aspect of the invention, all other variables are as originally defined with respect to formula I.

Another aspect of the invention that is of interest relates to a compound of formula I or a pharmaceutically acceptable salt or solvate thereof wherein $R^2$ represents $C_{1-10}$alkyl or phenyl optionally substituted with $C_{1-10}$alkyl or $OC_{1-6}$alkyl, said groups being optionally substituted with 1-5 halo groups up to perhalo. Within this aspect of the invention, all other variables are as originally defined with respect to formula I.

Another aspect of the invention that is of interest relates to a compound of formula I or a pharmaceutically acceptable salt or solvate thereof wherein $R^3$ represents $CH_2CH_2CO_2H$ or 5-tetrazolyl. Within this aspect of the invention, all other variables are as originally defined with respect to formula I.

Another aspect of the invention that is of interest relates to a compound of formula I or a pharmaceutically acceptable salt or solvate thereof wherein each $R^1$ is selected from the group consisting of: (a) H, halo, CN, $NR^6R^7$, with $R^6$ and $R^7$ representing H or $C_{1-6}$alkyl; (b) $C_{1-6}$alkyl, $OC_{1-6}$alkyl and $SC_{1-6}$alkyl, each optionally substituted with 1-5 halo groups; and (c) aryl optionally substituted with 1-4 halo groups or 1-2 members selected from $C_{1-6}$alkyl, $OC_{1-6}$alkyl, $haloC_{1-6}$alkyl and $OC_{1-6}$haloalkyl. Within this aspect of the invention, all other variables are as originally defined with respect to formula I.

Another aspect of the invention that is of interest relates to a compound of formula I or a pharmaceutically acceptable salt or solvate thereof wherein $R^8$ represents H, halo, $C_{1-3}$alkyl, $haloC_{1-3}$alkyl $OC_{1-3}$alkyl or $OhaloC_{1-3}$alkyl. Within this aspect of the invention, all other variables are as originally defined with respect to formula I.

Another aspect of the invention that is of particular interest relates to a compound of formula I or a pharmaceutically acceptable salt or solvate thereof wherein $R^8$ represents H or halo. Within this aspect of the invention, all other variables are as originally defined with respect to formula I.

Another aspect of the invention that is of interest relates to a compound of formula I or a pharmaceutically acceptable salt or solvate thereof wherein:

A represents phenyl;

X is absent or represents $CH_2$;

Y is absent or is selected from the group consisting of; NH and $CH_2$;

each $R^1$ is selected from the group consisting of: (a) H, halo, CN, $NR^6R^7$, with $R^6$ and $R^7$ representing H or $C_{1-6}$alkyl; (b) $C_{1-6}$alkyl, $OC_{1-6}$alkyl and $SC_{1-6}$alkyl, each optionally substituted with 1-5 halo groups; and (c) aryl optionally substituted with 14 halo groups or 1-2 members selected from $C_{1-6}$alkyl, $OC_{1-6}$alkyl, $haloC_{1-6}$alkyl and $OC_{1-6}$haloalkyl;

$R^2$ represents $C_{1-10}$alkyl or phenyl optionally substituted with $C_{1-10}$alkyl or $OC_{1-6}$alkyl, said groups being optionally substituted with 1-5 halo groups up to perhalo;

$R^3$ represents $CH_2CH_2CO_2H$ or 5-tetrazolyl, and $R^8$ represents H or halo, and $R^8$ represents H or halo. Within this aspect of the invention, all other variables are as originally defined with respect to formula I.

Another aspect of the invention that is of interest relates to a compound of formula I or a pharmaceutically acceptable salt or solvate thereof wherein:

A represents phenyl;

X is O;

Y is absent or is selected from the group consisting of; NH and $CH_2$;

each $R^1$ is selected from the group consisting of: (a) H, halo, CN, $NR^6R^7$, with $R^6$ and $R^7$ representing H or $C_{1-6}$alkyl; (b) $C_{1-6}$alkyl, $OC_{1-6}$alkyl and $SC_{1-6}$alkyl, each optionally substituted with 1-5 halo groups; and (c) aryl optionally substituted with 14 halo groups or 1-2 members selected from $C_{1-6}$alkyl, $OC_{1-6}$alkyl, $haloC_{1-6}$alkyl and $OC_{1-6}$haloalkyl;

$R^2$ represents $C_{1-10}$alkyl or phenyl optionally substituted with $C_{1-10}$alkyl or $OC_{1-6}$alkyl, said groups being optionally substituted with 1-5 halo groups up to perhalo;

$R^3$ represents $CH_2CH_2CO_2H$ or 5-tetrazolyl and $R^8$ represents H or halo. Within this aspect of the invention, all other variables are as originally defined with respect to formula I.

Another aspect of the invention that is of particular interest relates to the compounds of formula I shown in the examples and tables contained herein.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a mammalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, and a compound selected from the group consisting of:

(a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics, and GLP-1 receptor agonists; (h) GIP,GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents excluding glucocorticoids; and (o) protein tyrosine phosphatase-1B (PTP-IB) inhibitors, said compounds being administered to the patient in amounts that are effective to treat said condition.

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment therapeutically effective amounts of a compound of formula I as described above and an HMG-CoA reductase inhibitor.

Another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin.

Even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin selected from the group consisting of: lovastatin, simvastatin, pravastatin, fluvastatin, atorvastatin, itavastatin, ZD4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics and GLP-1 receptor agonists; (h) GIP, GIP mimetics and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; and (3) a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 2.0 g per day, preferably about 1 mg to about 500 mg, in single or divided doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet contains from about 1 mg to about 1.0 g of the active ingredient and each cachet or capsule contains from about 1 to about 500 mg of the active ingredient.

The following are examples of pharmaceutical dosage forms containing a compound of Formula I:

| Injectable Suspension (im.) | mg/mL |
|---|---|
| Compound of Formula 1 | 10.0 |
| Methylcellulose | 5.0 |
| Tween 80 | 0.5 |
| Benzyl alcohol | 9.0 |
| Benzalkonium chloride | 1.0 |
| Water for injection | t.d. 1.0 mL |

| Tablet | Mg/tablet |
|---|---|
| Compound of Formula 1 | 25.0 |
| Microcrystalline Cellulose | 415 |
| Povidone | 14.0 |
| Pregelatinized Starch | 4.35 |
| Magnesium Stearate | 2.5 |
| Total | 500 mg |

| Capsule | mg/capsule |
|---|---|
| Compound of Formula 1 | 25.0 |
| Lactose | 735 |
| Mg Stearate | 1.5 |
| Total | 600 mg |

| Aerosol | Per Canister |
|---|---|
| Compound of Formula 1 | 250 mg |
| Lecithin, NF Liq. Conc. | 1.2 mg |
| Trichloromethane, NF | 4.025 g |
| Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e.g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DPP-IV inhibitors, (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: (1) a compound according to formula I, (2) a compound selected from the group consisting of: (a) DPP-IV inhibitors; (b) insulin sensitizers selected from the group consisting of (i) PPAR agonists and (ii) biguanides; (c) insulin and insulin mimetics; (d) sulfonylureas and other insulin secretagogues; (e) a-glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; and (3) a pharmaceutically acceptable carrier.

The compounds of formula I can be synthesized in accordance with the general schemes provided below, taking into account the specific examples that are provided. Throughout the synthesis schemes, abbreviations are used with the following meanings unless otherwise indicated:

| | |
|---|---|
| AcOH = acetic acid | BOP = benzotriazol-1-yloxy-tris(dimethylamino)-phosphonium hexafluorophosphate |
| Bu = butyl, t-Bu = t-butyl | Bn and Bnzl = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DIAD = diisopropyl-azodicarboxylate |
| DMAP = 4-Dimethylaminopyridine | DME = Dimethoxyethane |

-continued

| | |
|---|---|
| EtOAc = ethyl acetate | DMF = N,N-dimethylformamide |
| eq. = equivalent(s) | EtOH = ethanol |
| Py, Pyr = pyridyl | THF = Tetrahydrofuran |
| HMPA = Hexamethylphosphoramide | FAB-mass spectrum = Fast atom bombardment-mass spectroscopy |
| HOAc = acetic acid | HPLC = High pressure liquid chromatography |
| HOBT, HOBt = Hydroxybenztriazole | IPA = isopropyl alcohol |
| Me = methyl | LAH = Lithium aluminum hydride |
| LDA = lithium diisopropylamide | LHMDS = lithium hexamethyl disilazide |
| PBS = phosphate buffer saline | MeOH = methanol |
| Ph = phenyl | TFA = Trifluoroacetic acid |
| $C_6H_{11}$ = cyclohexyl | $NMe_2$ = dimethylamino |
| iPr = isopropyl | 2ClPh = 2-chlorophenyl |
| 2,4-diClPh = 2,4-dichlorophenyl | |

Compounds of the present invention may be prepared according to the methodology outlined in the following general synthetic schemes.

In one embodiment of the present invention, the compounds (I) may be prepared from intermediate II (vide infra),

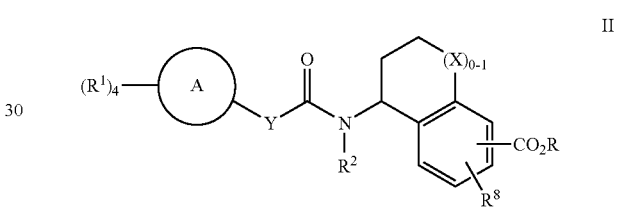

where R, $R^2$, X and Y are as defined above and R represents an alkyl group.

Compounds II can be prepared using a variety of methods which will become apparent to those of ordinary skill from the teachings herein, one such route being illustrated in Scheme 1. Bromo ketone 1 is carbonylated with carbon monoxide and an alcohol such as n-butanol at 115° C. or below and atmospheric pressure for 2 h in the presence of a tertiary amine such as diethylisopropylamine (DIEA) and a catalytic amount of palladium such as dichloro bis(triphenylphosphine) palladium (*J. Org. Chem.*, 1974, 39, 3318). Alternatively, hydroxyl ketone 2, which may be commercially available or readily prepared (*J. Org. Chem.*, 1994, 59, 1216), is used instead when bromo ketone 1 is not commercially available. Hydroxy ketone 2 is treated with trifluoromethanesulfonic anhydride in the presence of a base such as triethylamine in a nonpolar aprotic solvent such as dichloromethane at temperatures of from −78° C. to 25° C. Carbonylation of the resulting triflate is carried out with carbon monoxide at atmospheric pressure and a polar aprotic solvent such as N,N-dimethylformide (DMF) at 50° C. in the presence of an alcohol such as methanol, a tertiary base such as triethylamine and a catalytic amount of palladium complex (palladium acetate and 1,1'-bis(diphenylphosphineo)ferrocene). This reaction is described in detail in *Tetrahedron Lett., Vol. 27*, pg 3931, 1986. Ketone ester 3 is converted to amino ester 4 by reductive amination. This can be achieved in the presence of titanium(IV) isopropoxide and sodium borohydride (*J. Chem. Soc. Perkin Trans.* 1, 1998, 2527) in a polar solvent such as ethanol at ambient temperature for 16-24 h. In the case of that amine $R^2NH_2$ is an aniline, reductive amination can be affected simply with decaborane (*J. Chem. Soc. Perkin Trans.* 1, 2000, 145) in a polar solvent such as methanol.

SCHEME 1

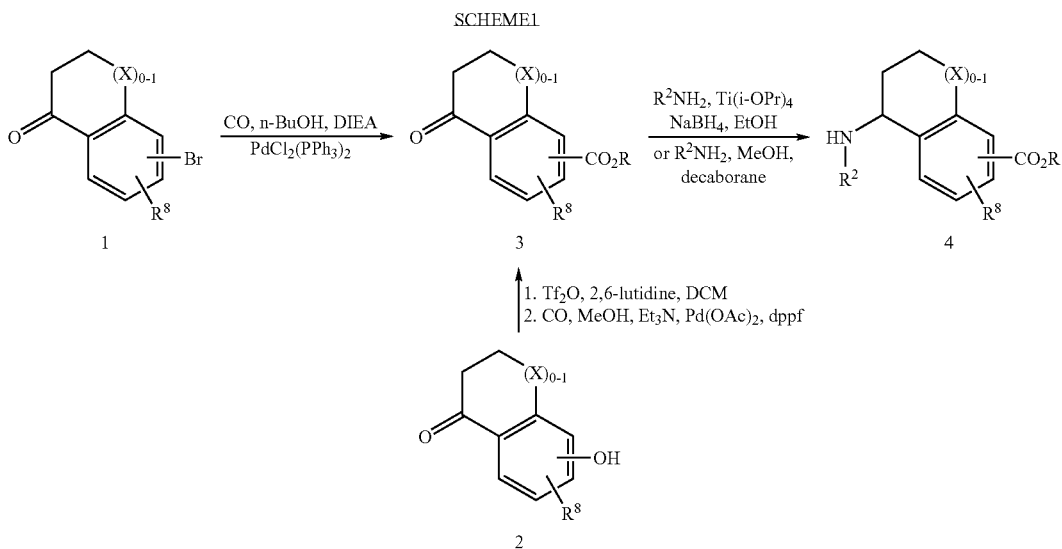

Preparation of intermediate II is illustrated in Scheme 2. In the case where Y=NH, amino ester 4 is treated with isocyanate 5 in the absence of base in a polar aprotic solvent such as tetrahydrofuran (THF) at ambient temperature. In the case where Y=CH$_2$ or is absent, coupling of carboxylic acid 6 with amino ester 4 is achieved using 1-ethyl-3-(3-dimethylaminopropyl)-carbodiimide (EDC), 1-hydroxybenzotriazole (HOBt), and a base, generally diisopropylethylamine, in a solvent such as DMF or methylene chloride for 6 to 18 hours at ambient temperature to yield intermediate II. Other peptide coupling conditions may also be used. When the corresponding acyl chloride 7 is used, acylation of amino ester 4 is achieved in a solvent such as dichloromethane with a base such as DIEA in the presence of a catalytic amount of dimethylaminopyridine (DMAP). Intermediate II contains a chiral center and the enantiomers can be resolved at this point by HPLC using a homochiral stationary phase. Alternatively, chiral separation can be achieved at an earlier stage and it will facilitate the synthetic process. This is achieved by converting amino ester 4 to carbamate 8 by treating with di-tert-butyl dicarbonate in a solvent such as dichloromethane with a base such as triethylamine and a catalytic amount of DMAP at ambient temperature for 18 h. The enantiomers of carbamate 8 are resolved by chiral HPLC. Optically pure amino ester 4 is obtained by deprotection of the BOC group with an acid such as trifluoroacetic acid in dichloromethane at ambient temperature for 0.5-3 h.

SCHEME 2

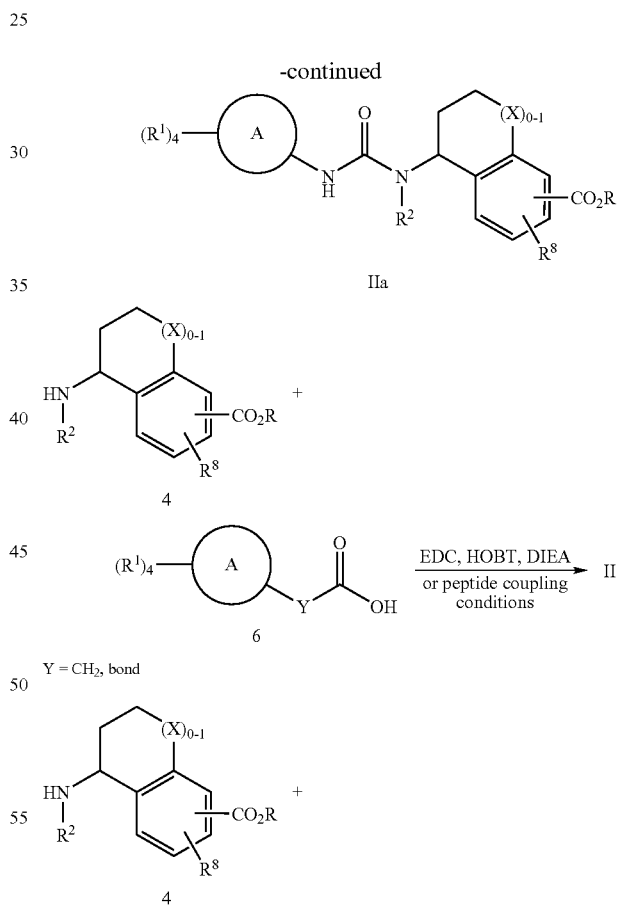

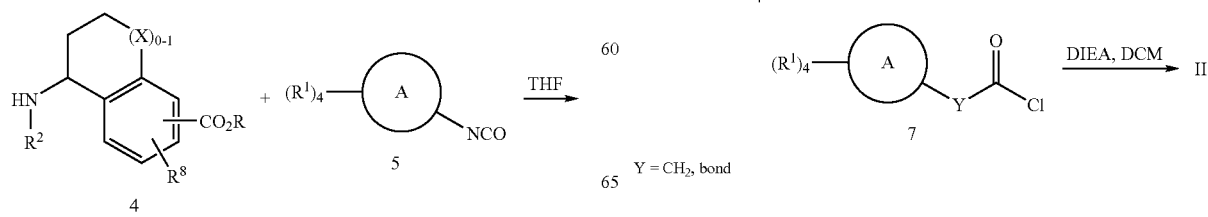

SCHEME 3

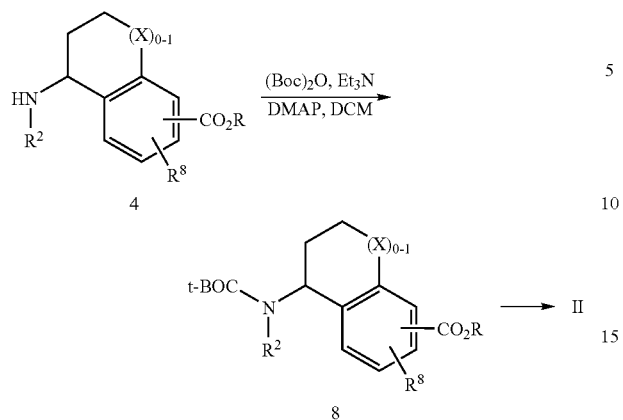

-continued

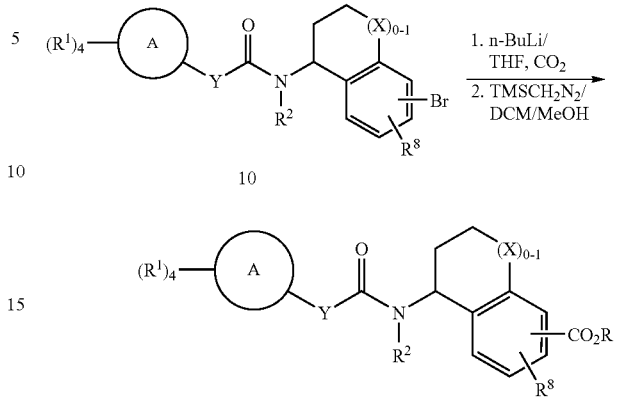

An alternate route to intermediate II involves carbonylation at a later stage as shown in Scheme 4. Reductive amination of bromo ketone 1 using method described in Scheme 1 gives rise to amine intermediate 9, which is further elaborated to intermediate 10 using methods detailed in Scheme 2. Carbonylation is achieved by treating bromide 10 with a base such as butyl lithium in a polar aprotic solvent such as THF at −78° C. and then reacting with carbon dioxide at −78° C. to 0° C. Esterification of the resulting carboxylic acid, for example, with trimethylsilyl diazomethane ($TMSCH_2N_2$) in dichloromethane and methanol, gives rise to intermediate II, which is resolved on chiral HPLC.

SCHEME 4

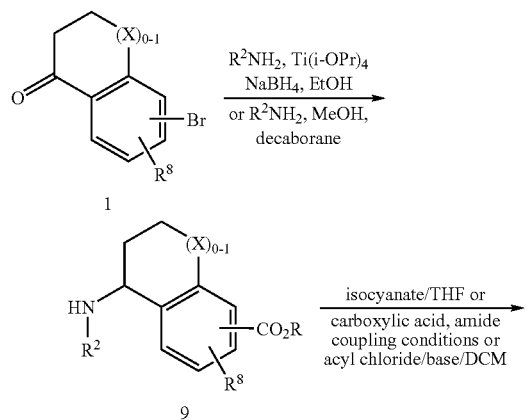

Preparation of the desired compounds I is then achieved by saponification of the ester II using a base such as aqueous lithium or sodium hydroxide in a polar solvent such as tetrahydrofuran, methanol, ethanol or a mixture of similar solvents, Scheme 5. Coupling of the resulting carboxylic acid with an amine, generally 5-aminotetrazole 11 or a beta alanine derivative 12 which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield the compounds Ia, and following deprotection, Ib. Other peptide coupling conditions may also be used. The product is purified from unwanted side products by recrystallization, trituration, preparative thin layer chromatography, flash chromatography on silica gel as described by W. C. Still et al, *J. Org. Chem.*, 43, 2923, (1978), or HPLC. Compounds purified by HPLC may be isolated as the corresponding salt. Purification of intermediates is achieved in the same manner. As will be understood by those skilled in the art, for the preparation of enantiomerically pure compounds, enantiomerically pure starting materials should be used.

Scheme 5

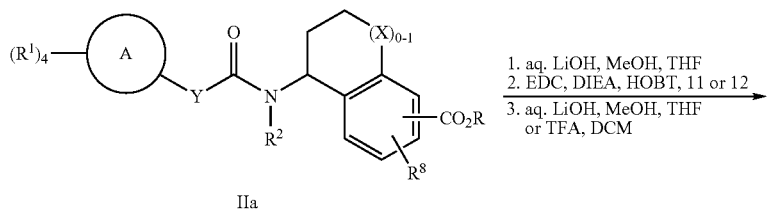

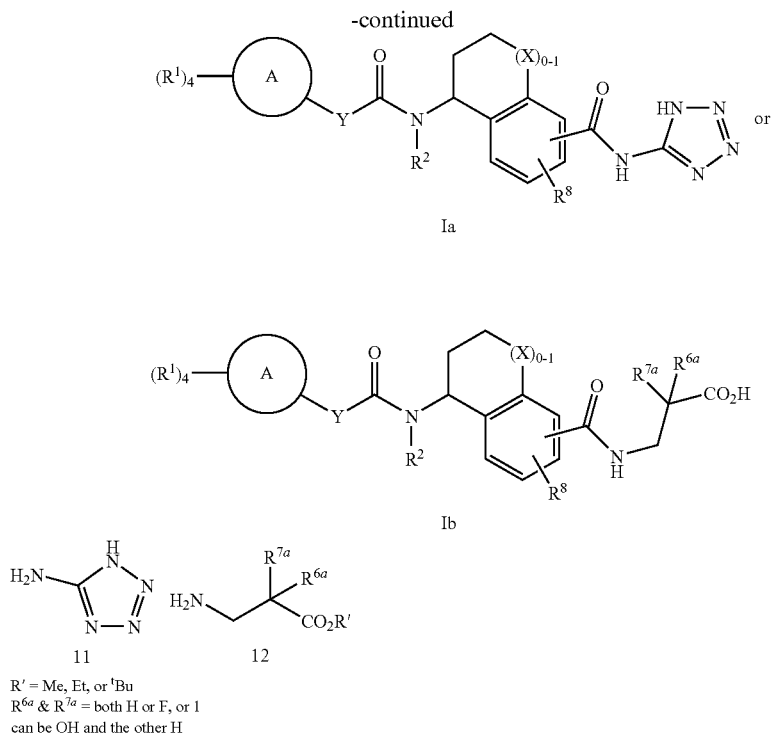

In some cases, the product from the reactions described in Scheme 5 will be further modified. These manipulations may include, but are not limited to substitution, reduction, oxidation, alkylation, acylation, and hydrolysis reactions, which are commonly known to those skilled in the art. One such modification is saponification of a methyl or removal of a tert butyl ester, as shown, this is achieved using a base such as aqueous lithium or sodium hydroxide in a polar solvent such as tetrahydrofuran, methanol, ethanol or a mixture of similar solvents or by treatment with trifluoroacetic acid in methylene chloride at ambient temperatures for 0.5-3 h.

The following examples are provided so that the invention might be more fully understood. They should not be construed as limiting the invention in any way.

Intermediate 1

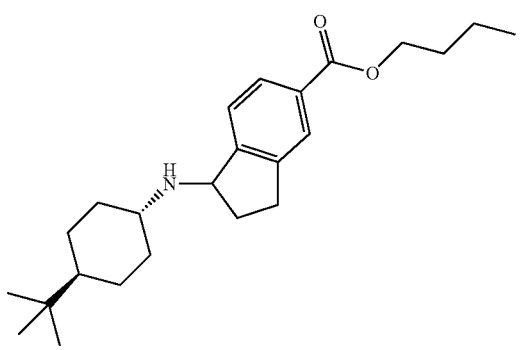

Step A. Butyl 1-oxoindane-5-carboxylate

A mixture of 5-bromo-1-indanone (5.0 g, 23.7 mmol), DIEA (14.4 mL, 82.9 mmol) and $PdCl_2(PPh_3)_2$ in n-BuOH (50 mL) was purged with carbon monoxide for 5 min and then stirred under a CO balloon at 115° C. for 2 h. The reaction mixture was allowed to cool to room temperature and filtered through Celite. Solvent evaporation in vacuo followed by filtration on a short column of silica gel and eluted with $CH_2Cl_2$ gave the crude product. Chromatography (10% EtOAc in Hexane) afforded butyl 1-oxoindane-5-carboxylate. HPLC/MS: m/z=233.1 (M+1), $R_t$=3.55 min. $^1$H NMR ($CDCl_3$): δ 8.18 (1H, s), 8.06 (1H, d, J=8.0 Hz), 7.82 (1H, d, J=8.0 Hz), 4.39 (2H, t, J=6.5 Hz), 3.23 (2H, t, J=6.0 Hz), 2.78 (2H, t, J=6.0 Hz), 1.81 (1H, m), 1.52 (2H, m), 1.02 (3H, t, J=7.0 Hz).

Step B. Butyl 1-[(trans-4-tert-butylcyclohexyl)amino]indane-5-carboxylate (racemic)

A mixture of butyl 1-oxoindane-5-carboxylate (5.0 g, 21.5 mmol), titanium (IV) isopropoxide (7.04 mL, 23.7 mmol), 4-tert-butylcyclohexyl amine (6.68 g, 43.0 mmol) in absolute ethanol (60 mL) was stirred under nitrogen at room temperature for 18 h. Sodium borohydride (1.22 g, 32.2 mmol) was then added and the resulting mixture was stirred for an additional 24 h at room temperature. The reaction was quenched by pouring into aqueous ammonia (2N, 200 mL). The resulting inorganic precipitate was filtered off through Celite and washed with $CH_2Cl_2$ (300 mL). The organic layer was separated and the remaining aqueous layer was extracted once with $CH_2Cl_2$ (150 mL). The combined organic extracts were dried over $Na_2SO_4$, filtered and concentrated. Chromatography (8% to 15% EtOAc in Hexane) afforded butyl 1-[(trans-4-tert-butylcyclohexyl)amino]indane-5-carboxylate and the corresponding cis product (less polar than the trans amine).

HPLC/MS: m/z=372.3 (M+1), $R_t$=2.14 min. $^1$H NMR (CDCl$_3$): δ 7.93 (1H, d, J=8.0 Hz), 7.92 (1H, s), 7.43 (1H, d, J=8.0 Hz), 4.41 (1H, t, J=6.5 Hz), 4.35 (2H, t, J=6.5 Hz), 3.05 (1H, ddd, J=4.0 Hz, 8.0 Hz, 16.0 Hz), 2.86 (1H, dt, J=8.0 Hz, 16.0 Hz), 2.65 (1H, m), 2.51 (1H, m), 2.10 (1H, m), 2.02 (1H, m), 1.88-1.76 (5H, m), 1.56-1.48 (2H, m), 1.22-1.01 (8H, m), 0.90 (9H, s).

Step C. Butyl 1-[(trans-4-tert-butylcyclohexyl)amino]indane-5-carboxylate (chiral)

To a solution of butyl 1-[(trans-4-tert-butylcyclohexyl)amino]indane-5-carboxylate (1.0 g, 2.8 mmol) in CH$_2$Cl$_2$ (50 mL) was added Et$_3$N (2.0 mL, 14.3 mmol), BOC$_2$O (3.1 mL, 13.5 mmol) and catalytic amount of DMAP. After stirring at room temperature for 18 h, the reaction was quenched with saturated aqueous NaHCO$_3$ (50 mL). The layers were separated and the aqueous layer was extracted once with EtOAc (50 mL). The combined organic layers were dried over Na$_2$SO$_4$, filtered and concentrated. Chromatography (5% EtOAc in Hexane) gave butyl 1-[(tert-butoxycarbonyl)(trans-4-tert-butylcyclohexyl)amino]indane-5-carboxylate. HPLC/MS: m/z=416.3 (M−56+1), 438.3 (M−56+23), $R_t$=3.07 min. $^1$H NMR (CDCl$_3$): δ 7.90 (1H, d, J=8.5 Hz), 7.89 (1H, s), 7.16 (1H, m), 4.75 (1H, br s), 4.35 (2H, t, J=6.5 Hz), 4.19 (1H, br s), 3.10-3.05 (1H, m), 2.97-2.87 (1H, m), 2.36 (2H, m), 1.91-1.77 (5H, m), 1.52 (2H, m), 1.07-1.00 (8H, m), 0.90 (9H, s), 0.89 (9H, s).

Resolution of the above racemic compound on chiral HPLC (ChiralPak AD column, 10% IPA in n-Heptane) afforded enantiomers A ($R_t$=10.90 min) and B ($R_t$=13.84 min). t-BOC group was removed by treating the compound with 20% TFA in CH$_2$Cl$_2$ for 30 min. HPLC/MS: m/z=372.3 (M+1), $R_t$=2.25 min.

Intermediate 2

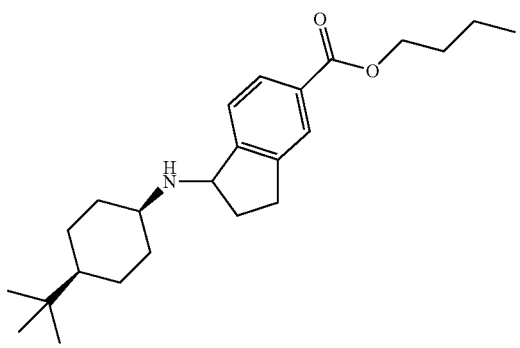

Butyl 1-[(cis-4-tert-butylcyclohexyl)amino]indane-5-carboxylate (racemic)

Butyl 1-[(cis-4-tert-butylcyclohexyl)amino]indane-5-carboxylate was isolated as a by product as described (Step B, Intermediate 1). HPLC/MS: m/z=372.3 (M+1), $R_t$=2.14 min. $^1$H NMR (CDCl$_3$): δ 7.94 (1H, d, J=8.0 Hz), 7.92 (1H, s), 7.43 (1H, d, J=8.0 Hz), 4.35 (2H, t, J=6.5 Hz), 4.30 (1H, t, J=7.5 Hz), 3.11 (1H, m), 3.05 (1H, ddd, J=3.5 Hz, 8.5 Hz, 16.0 Hz), 2.86 (1H, dt, J=8.0 Hz, 16.0 Hz), 2.52 (1H, m), 1.98 (1H, m), 1.85-1.76 (5H, m), 1.62-1.41 (8H, m), 1.10-1.01 (3H, m), 0.92 (9H, s).

Intermediate 3

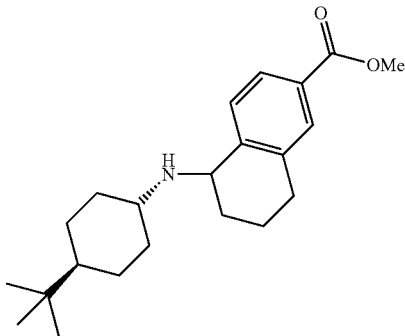

Step A. Methyl 5-oxo-5,6,7,8-tetrahydronaphthalene-2-carboxylate

To a solution of 6-hydroxy 1-tetralone (3.7 g, 22.7 mmol) and 2,6-lutidine (12.2 mL, 102.5 mmol) in dry CH$_2$Cl$_2$ (50 mL) at 0° C. was slowly added triflic anhydride (4.0 mL, 34.0 mmol) and the reaction mixture was stirred at 0° C. for 1 h. H$_2$O (50 mL) was then added to quench the reaction. After stirring for 15 min at room temperature, the mixture was diluted with CH$_2$Cl$_2$ (100 mL) and the layers were separated. The organic layer was washed once with 10% aqueous NaHCO$_3$ solution (100 mL), once with brine (100 mL), dried over Na$_2$SO$_4$, filtered and concentrated. Chromatography (5% to 8% EtOAc in Hexane) gave 6-triflate 1-tetralone. HPLC/MS: m/z=295.1 (M+1), $R_t$=3.54 min. $^1$H NMR (CDCl$_3$): δ 8.17 (1H, d, J=8.50 Hz), 7.26-7.23 (2H, m), 3.06 (2H, t, J=6.0 Hz), 2.73 (2H, t, J=6.0 Hz), 2.22 (2H, qn, J=6.0 Hz).

A mixture of 6-triflate 1-tetralone (4.8 g, 16.3 mmol), Et$_3$N (4.5 mL, 32.6 mmol), Pd(OAc)$_2$ (0.11 g, 0.49 mmol) and dppf (0.54 g, 0.98 mmol) in dry MeOH (10 mL) was purged with carbon monoxide for 5 min and then stirred under a CO balloon at 60° C. for 2 h. The reaction mixture was allowed to cool to room temperature, diluted with brine (100 mL) and extraction with Et$_2$O (3×50 mL). The combined organic layers were washed once with 1N aqueous HCl, once with brine, dried over Na$_2$SO$_4$, filtered and concentrated. Chromatography (8% EtOAc in Hexane) afforded methyl 5-oxo-5,6,7,8-tetrahydronaphthalene-2-carboxylate as a white solid. HPLC/MS: m/z=205.1 (M+1), $R_t$=3.01 min. $^1$H NMR (CDCl$_3$): δ 8.08 (1H, d, J=8.0 Hz), 7.95 (1H, s), 7.94 (1H, d, J=8.0 Hz), 3.96 (3H, s), 3.04 (2H, t, J=6.0 Hz), 2.71 (2H, t, J=6.0 Hz), 2.18 (2H, qn, J=6.0 Hz).

Step B. Methyl 5-[(trans-4-tert-butylcyclohexyl)amino]-5,6,7,8-tetrahydronaphthalene-2-carboxylate A mixture of methyl 5-oxo-5,6,7,8-tetrahydronaphthalene-2-carboxylate (1.0 g, 4.9 mmol), titanium (IV) isopropoxide (2.8 mL, 9.8 mmol), 4-tert-butylcyclohexyl amine (1.5 g, 9.8 mmol) in absolute ethanol (75 mL) was stirred under nitrogen at room temperature for 7 h. Sodium borohydride (0.28 g, 7.4 mmol) was then added and the resulting mixture was stirred for an additional 18 h at room temperature. The reaction was quenched by pouring into aqueous ammonia (2N, 100 mL). The resulting inorganic precipitate was filtered off through Celite and washed with CH$_2$Cl$_2$ (100 mL). The organic layer was separated and the remaining aqueous layer was extracted once with CH$_2$Cl$_2$ (50 mL). The combined organic extracts were dried over Na$_2$SO$_4$, filtered and concentrated. Chromatography (15% EtOAc in Hexane) afforded methyl 5-[(trans-4-tert-butylcyclohexyl)amino]-5,6,7,8-tetrahydronaphthalene-2-carboxylate and the corresponding cis product (less polar). HPLC/MS: m/z=344.3 (M+1), R$_t$=2.84 min. $^1$H NMR (CDCl$_3$): δ 7.83 (1H, d, J=8.05 Hz), 7.79 (1H, s), 7.47 (1H, d, J=8.5 Hz), 3.94 (3H, s), 2.89 (1H, m), 2.77 (1H, m), 2.62 (1H, m), 2.15 (1H, m), 2.01-1.91 (3H, m), 1.86-1.77 (4H, m), 1.56 (2H, m), 1.23-1.02 (4H, m), 0.90 (9H, s).

Intermediate 4

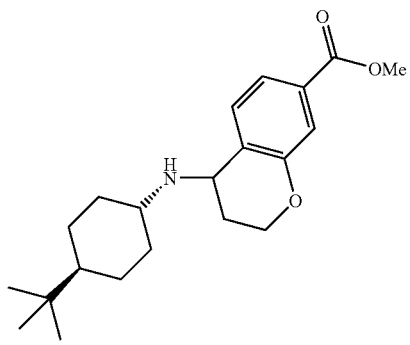

Step A. Methyl 4-oxochromane-7-carboxylate

Methyl 4-oxochromane-7-carboxylate was prepared by following literature procedure (*J. Org Chem.* 1994, 59, 1216-1218). HPLC/MS: m/z=207.1 (M+1), R$_t$=1.80 min. $^1$H NMR (CDCl$_3$): δ 7.98 (1H, d, J=8.5 Hz), 7.68-7.67 (2H, m), 4.61 (2H, t, J=6.5 Hz), 3.97 (3H, s), 2.89 (2H, t, J=6.5 Hz).

Step B. Methyl 4-[(trans-4-tert-butylcyclohexyl)amino]chromane-7-carboxylate

A mixture of methyl 4-oxochromane-7-carboxylate (2.06 g, 9.99 mmol), titanium (IV) isopropoxide (3.27 mL, 10.99 mmol), 4-tert-butylcyclohexyl amine (3.10 g, 19.98 mmol) in absolute ethanol (40 mL) was stirred under nitrogen at room temperature for 17 h. Sodium borohydride (0.45 g, 11.99 mmol) was then added and the resulting mixture was stirred for an additional 3 h at room temperature. The reaction was quenched by pouring into aqueous ammonia (2N, 100 mL). The resulting inorganic precipitate was filtered off through Celite and washed with CH$_2$Cl$_2$ (200 mL). The organic layer was separated and the remaining aqueous layer was extracted once with CH$_2$Cl$_2$ (100 mL). The combined organic extracts were dried over Na$_2$SO$_4$, filtered and concentrated. Chromatography (15% EtOAc in Hexane) afforded methyl 4-[(trans-4-tert-butylcyclohexyl)amino]chromane-7-carboxylate and the corresponding cis product (less polar). HPLC/MS: m/z=346.3 (M+1), R$_t$=1.95 min. $^1$H NMR (CDCl$_3$): δ 7.57 (1H, dd, J=2.0 Hz, 8.0 Hz), 7.50 (1H, d, J=2.0 Hz), 7.35 (1H, d, J=8.0 Hz), 4.36 (1H, dt, J=2.5 Hz, 11.0 Hz), 4.27 (11H, dt, J=4.0 Hz, 11.0 Hz), 3.97 (1H, t, J=4.0 Hz), 3.93 (3H, s), 2.64-2.58 (1H, m), 2.18-2.15 (1H, m), 2.11-2.04 (1H, m), 1.97-1.91 (2H, m), 1.91-1.84 (2H, m), 1.22-1.02 (5H, m), 0.92 (9H, s).

Intermediate 5

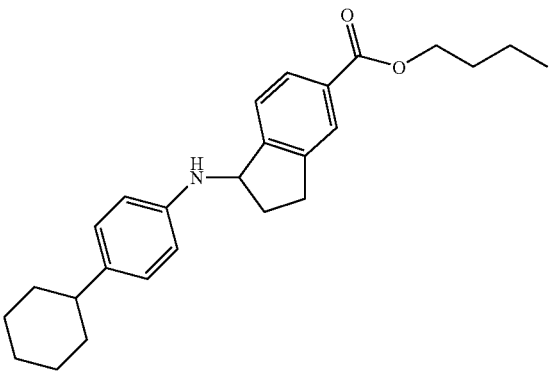

Butyl 1-[(4-cyclohexylphenol)amino]indane-5-carboxylate

A mixture of butyl 1-oxoindane-5-carboxylate (2.00 g, 8.60 mmol), 4-cyclohexylaniline (2.28 g, 13.00 mmol), decaborane (0.32 g, 2.60 mmol) in dry MeOH (30 mL) was stirred under nitrogen for 60 h. Yellow precipitates were collected by filtration and washed with MeOH (3×5 mL) to give butyl 1-[(4-cyclohexylphenyl)amino]indane-5-carboxylate as a white solid. HPLC/MS: m/z=392.6 (M+1), R$_t$=4.97 min. $^1$H NMR (CDCl$_3$): δ 8.00 (1H, s), 7.97 (1H, d, J=8.0 Hz), 7.48 (1H, d, J=8.0 Hz), 7.14 (2H, d, J=8.0 Hz), 6.74 (2H, d, J=8.0 Hz), 5.07 (1H, t, J=7.0 Hz), 4.39 (2H, t, J=6.5 Hz), 3.92 (1H, br s), 3.12-3.07 (1H, m), 3.00-2.94 (1H, m), 2.72-2.66 (1H, m), 2.52-2.47 (1H, m), 2.02-1.80 (8H, m), 1.60-1.31 (7H, m), 1.08 (3H, t, J=7.5 Hz).

Intermediate 6

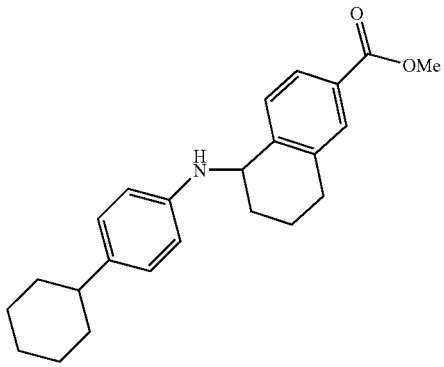

Methyl 5-[(4-cyclohexylphenyl)amino]-5,6,7,8-tetrahydronaphthalene-2-carboxylate A mixture of methyl 5-oxo-5,6,7,8-tetrahydronaphthalene-2-carboxylate (1.2 g, 5.9 mmol), 4-cyclohexylaniline (2.1 g, 11.8 mmol), decaborane (0.22 g, 1.8 mmol) in dry MeOH (20 mL) was stirred under nitrogen for 4 h. Solvent evaporation and chromatography (5% to 20% EtOAc in Hexane) gave methyl 5-[(4-cyclohexylphenyl)amino]-5,6,7,8-tetrahydronaphthalene-2-carboxylate as a yellow solid. HPLC/MS: m/z=364.2 (M+1), R$_t$=2.83 min. $^1$H NMR (CDCl$_3$): δ 7.86 (1H, s), 7.85 (1H, d, J=7.5 Hz), 7.54 (1H, d, J=7.5 Hz), 7.11 (2H, d, J=8.5 Hz), 6.68 (2H, d, J=8.5 Hz), 4.66 (1H, t, J=5.5 Hz), 3.96 (3H, s), 3.79 (1H, br s), 2.97-2.82 (2H, m), 2.46 (1H, m), 2.10-1.78 (9H, m), 1.44 (4H, m), 1.30 (1H, m).

Intermediate 7

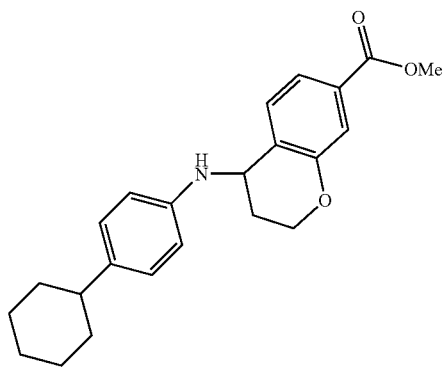

Methyl 4-[(4-cyclohexylphenyl)amino]chromane-7-carboxylate

A mixture of methyl 4-oxochromane-7-carboxylate (1.50 g, 7.27 mmol), 4-cyclohexylaniline (2.55 g, 14.55 mmol), decaborane (0.27 g, 2.18 mmol) in dry MeOH (15 mL) was stirred under nitrogen for 60 h. Solvent evaporation in vacuo and chromatography (8% EtOAc in Hexane) gave methyl 4-[(4-cyclohexylphenyl)amino]chromane-7-carboxylate as a slightly yellow solid. HPLC/MS: m/z=365.2 (M+1), $R_t$=2.56 min. $^1$H NMR (CDCl$_3$): δ 7.59 (1H, dd, J=2.0 Hz, 8.0 Hz), 7.56 (1H, d, J=2.0 Hz), 7.43 (1H, d, J=8.0 Hz), 7.12 (2H, d, J=8.5 Hz), 6.69 (2H, d, J=8.5 Hz), 4.68 (1H, t, J=4.5 Hz), 4.35-4.26 (2H, m), 3.95 (3H, s), 3.86 (1H, br s), 2.46 (1H, m), 2.20 (2H, dd, J=4.5 Hz, 10.5 Hz), 1.92-1.87 (4H, m), 1.80-1.77 (1H, m), 1.43 (4H, m), 1.29 (1H, m).

The racemic methyl 4-[(4-cyclohexylphenyl)amino]chromane-7-carboxylate was resolved on ChiralPak AD column with 15% IPA in n-Heptane to give enantiomer A (−), $R_t$=14.48 min and B (+), $R_t$=16.01 min.

Example 1/2

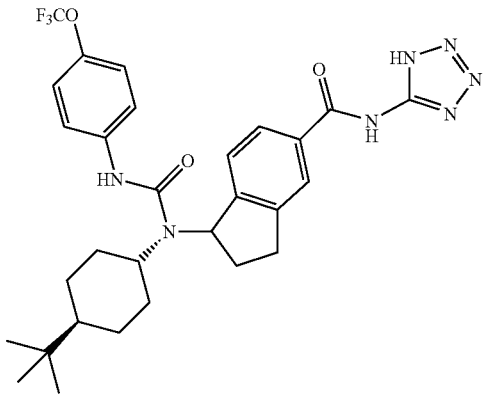

Step A. (5-Bromo-2,3-dihydro-1H-inden-1-yl)(trans-4-tert-butylcyclohexyl)amine

A mixture of 5-bromo-1-indanone (6.33 g, 30.0 mmol), titanium (IV) isopropoxide (17.8 mL, 60.0 mmol), 4-tert-butylcyclohexyl amine (9.32 g, 60.0 mmol) in absolute ethanol (200 mL) was stirred under nitrogen at room temperature for 8 h. Sodium borohydride (1.70 g, 45.0 mmol) was then added and the resulting mixture was stirred for an additional 18 h at room temperature. The reaction was quenched by pouring into aqueous ammonia (2N, 300 mL). The resulting inorganic precipitate was filtered off through Celite and washed with CH$_2$Cl$_2$ (300 mL). The organic layer was separated and the remaining aqueous layer was extracted once with CH$_2$Cl$_2$ (100 mL). The combined organic extracts were dried over Na$_2$SO$_4$, filtered and concentrated. Chromatography (10% to 20% EtOAc in Hexane) afforded (5-bromo-2,3-dihydro-1H-inden-1-yl)(trans-4-tert-butylcyclohexyl). HPLC/MS: m/z=350.1, (M+1), $R_t$=3.01 min. $^1$H NMR (CDCl$_3$): δ 7.38 (1H, br s), 7.34 (1H, d, J=8.0 Hz), 7.24 (1H, d, J=8.0 Hz), 4.32 (1H, t, J=6.5 Hz), 3.00 (1H, ddd, J=5.0 Hz, 8.0 Hz, 16.0 Hz), 2.81 (1H, dt, J=8.0 Hz, 16.0 Hz), 2.61 (1H, m), 2.46 (1H, m), 2.08 (1H, m), 2.00 (1H, m), 1.86-1.78 (4H, m), 1.20-1.04 (4H, m), 0.90 (9H, s).

Step B. N-(5-bromo-2,3-dihydro-1H-inden-1-yl)-N-(trans-4-tert-butylcyclohexyl)-N'-[4-(trifluoromethoxy)phenyl]urea To a solution of (5-bromo-2,3-dihydro-1H-inden-1-yl)(trans-4-tert-butylcyclohexyl) (1.05 g, 3.0 mmol) in dry THF (30 mL) at 0° C. was added (4-trifluoromethoxy)phenyl isocyanate (0.45 mL, 3.0 mmol) and the reaction mixture was stirred at 0° C. for 15 min. Solvent evaporation and chromatography (5% EtOAc in Hexane) gave N-(5-bromo-2,3-dihydro-1H-inden-1-yl)-N-(trans-4-tert-butylcyclohexyl)-N'-[4-(trifluoromethoxy)phenyl]urea as an off-white solid. HPLC/MS: m/z=553.2, (M+1), $R_t$=2.98 min. $^1$H NMR (CDCl$_3$): δ 7.56 (1H, s), 7.47 (1H, d, J=8.0 Hz), 7.19 (1H, d, J=8.0 Hz), 7.06 (2H, d, J=8.5 Hz), 6.96 (2H, d, J=8.5 Hz), 5.88 (1H, s), 5.02 (1H, t, J=9.0 Hz), 4.44 (1H, t, J=12.0 Hz), 3.13 (1H, dd, J=8.0 Hz, 16.0 Hz), 2.97 (1H, dt, J=8.0 Hz, 16.0 Hz), 2.54-2.47 (1H, m), 2.42-2.33 (1H, m), 2.01-1.93 (2H, m), 1.64-1.52 (2H, m), 1.34-1.27 (2H, m), 1.02 (1H, m), 0.91 (9H, s).

Step C. Methyl 1-[(trans-4-tert-butylcyclohexyl)({[4-(trifluoromethoxy)phenyl]amino}carbonyl)amino]indane-5-carboxylate N-(5-bromo-2,3-dihydro-1H-inden-1-yl)-N-(trans-4-tert-butylcyclohexyl)-N'-[4-(trifluoromethoxy)phenyl]urea (2.67 g, 4.82 mmol) was azeotropically dried from toluene/CH$_2$Cl$_2$ (4:1, 3×10 mL) and placed under high vac for 2 h before use. It was then dissolved in dry THF (120 mL) and cooled to −78° C. under nitrogen. BuLi (12.1 mL, 1.6 M solution in hexane) was added slowly via a syringe and the reaction mixture was stirred at −78° C. for 30 min. Dry ice cubes were added and the cold bath was removed. The reaction mixture was allowed to warm up slowly to 0° C. and then poured into saturated NH$_4$Cl solution (100 mL). The resulting mixture was extracted with EtOAc (3×100 mL) and the combined organic layers were dried over Na$_2$SO$_4$, filtered and concentrated. Chromatography (30% to 50% EtOAc in Hexane) gave the corresponding carboxylic acid.

To a solution of 1-[(trans-4-tert-butylcyclohexyl)({[4-(trifluoromethoxy)phenyl]amino}carbonyl)amino]indane-5-carboxylic acid (0.78 g, 1.50 mmol) in MeOH/CH$_2$Cl$_2$ (1:1, 20 mL) was slowly added TMSCH$_2$N$_2$ until gas bubbling ceased and the yellow color sustained. Solvent evaporation and chromatography (10% EtOAc in Hexane) gave of the corresponding methyl ester. HPLC/MS: m/z=533.3, (M+1), $R_t$=3.02 min. $^1$H NMR (CDCl$_3$): δ 8.07 (1H, s), 8.02 (1H, d, J=8.0 Hz), 7.38 (1H, d, J=8.0 Hz), 7.01 (2H, t, J=8.5 Hz), 6.92 (1H, d, J=8.5 Hz), 5.82 (1H, s), 5.09 (1H, t, J=9.0 Hz), 4.43 (1H, br t), 3.98 (3H, s), 3.18 (1H, dd, J=9.0 Hz, 16.5 Hz), 3.00 (1H, dt, J=9.5 Hz, 18.5 Hz), 2.54 (1H, m), 2.42 (1H, m), 2.02 (2H, t, J=14.0 Hz), 1.95 (2H, d, J=11.0 Hz), 1.59 (2H, m), 1.33-1.26 (2H, m), 1.01 (1H, m), 0.90 (9H, s).

Methyl 1-[(trans-4-tert-butylcyclohexyl)({[4-(trifluoromethoxy)phenyl]amino}carbonyl)amino]indane-5-carboxylate (600 mg) was dissolved in EtOH/n-Heptane (2:8, 9 mL) and resolved on Chiral HPLC (ChiralCel OD column, 18% EtOH in n-Heptane) to give enantiomer A (fast moving component) and B (slow moving component).

Step D. 1-[(trans-4-tert-butylcyclohexyl)({[4-(trifluoromethoxy)phenyl]amino}carbonyl)amino]-N-1H-tetrazol-5-ylindane-5-carboxamide Enantiomer A or B (60 mg, 0.12 mmol) from Step C were treated with aqueous LiOH solution (1.0 M, 2 mL) in THF/MeOH (1:1, 4 mL) at room temperature for 18 h. The reaction mixture was acidified with aqueous 1N HCl until white precipitates started to appear. The resulting mixture was then diluted with brine (10 mL) and extracted with EtOAc (3×10 mL). The combined organic layers were dried over $Na_2SO_4$, filtered and concentrated. The residue was then divided into 3 portions and coupled respectively to 5-amino tetrazole (15 mg, 0.14 mmol), β-alanine methyl ester HCl salt (22 mg, 0.16 mmol) and α-hydroxy-β-alanine methyl ester HCl salt (17 mg, 0.11 mmol). All three coupling reactions were run with EDC (28 mg, 0.15 mmol), HOBt (20 mg, 0.15 mmol), DIEA (50 μL, 0.29 mmol) in dry DMF (3 mL) at room temperature for 18 h. The crude tetrazole product was purified on HPLC (Xterra $C_{18}$ column from Waters, 20% to 95% $CH_3CN$ in $H_2O$ containing 0.1% TFA over 12 min) and freeze-dried from 1,4-dioxane to give enantiomer A or enantiomer B of 1-[(trans-4-tert-butylcyclohexyl)({[4-(trifluoromethoxy)phenyl]amino}carbonyl)amino]-N-1H-tetrazol-5-ylindane-5-carboxamide. Enantiomer A: HPLC/MS: m/z=586.3 (M+1), $R_t$=4.17 min. $^1$H NMR (DMSO-$d_6$): δ 12.30 (1H, s), 8.38 (1H, s), 7.93 (1H, s), 7.88 (1H, d, J=8.0 Hz), 7.42 (2H, d, J=9.0 Hz), 7.19 (1H, d, J=8.0 Hz), 7.17 (2H, d, J=9.0 Hz), 5.02 (1H, br s), 3.08 (1H, m), 2.89 (1H, m), 2.40 (1H, m), 2.33 (1H, m), 2.01 (1H, m), 1.82 (6H, m), 1.20 (2H, m), 1.03 (1H, m), 0.87 (9H, s). Enantiomer B: HPLC/MS and $^1$H NMR (DMSO-$d_6$) are identical to those of enantiomer A.

Example 3/4

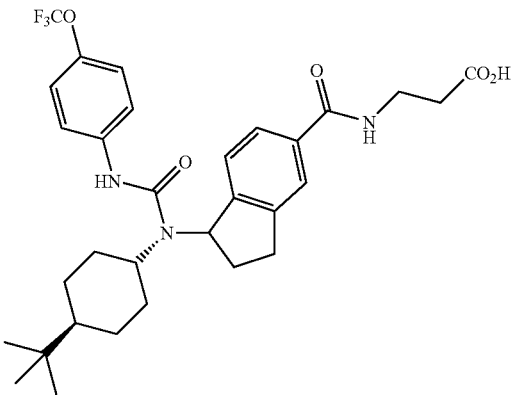

N-({1-[(trans-4-tert-butylcyclohexyl)({[4-(trifluoromethoxy)phenyl]amino}carbonyl)amino]-2,3-dihydro-1H-inden-5-yl}carbonyl)-β-alanine The reaction mixtures from β-alanine or α-hydroxy β-alanine as described above (Step D, Example 1/2) were diluted with saturated aqueous $NaHCO_3$ (10 mL) and extracted once with EtOAc (20 mL). The organic layer was washed with brine (2×10 mL), dried over $Na_2SO_4$, filtered and concentrated. Chromatography (35% EtOAc in Hexane for β-alanine and 50% EtOAc in Hexane for α-hydroxy β-alanine) gave the corresponding methyl esters. The methyl esters were saponified with aqueous LiOH (1.0 M, 2 mL) in THF/MeOH (1:1, 4 mL) at room temperature for 3 h. The reaction mixtures were acidified with aqueous 1N HCl until white precipitates just started to appear. It was then diluted with brine (10 mL) and extracted with EtOAc (3×10 mL). The combined organic layers were dried over $Na_2SO_4$, filtered, concentrated and freeze-dried from 1,4-dioxane without further purification to give enantiomer A or enantiomer B of N-({1-[(trans-4-tert-butylcyclohexyl)({[4-(trifluoromethoxy)phenyl]amino}carbonyl)amino]-2,3-dihydro-1H-inden-5-yl}carbonyl)-β-alanine. Enantiomer A: HPLC/MS: m/z=590.3 (M+1), $R_t$=4.07 min. $^1$H NMR (DMSO-$d_6$): δ 12.19 (1H, s), 8.41 (1H, t, J=5.5 Hz), 8.25 (1H, s), 7.66 (1H, s), 7.61 (1H, d, J=8.0 Hz), 7.40 (2H, d, J=9.5 Hz), 7.16 (2H, d, J=8.5 Hz), 7.12 (1H, d, J=8.0 Hz), 5.04 (1H, br s), 3.44 (2H, m), 3.04 (1H, m), 2.84 (1H, m), 2.51 (2H, m), 2.31 (2H, m), 1.94 (1H, m), 1.81 (6H, m), 1.14 (2H, m), 1.01 (1H, m), 0.86 (9H, s). Enantiomer B: HPLC/MS and $^1$H NMR (DMSO-$d_6$) are identical to those of enantiomer A.

Example 5/6

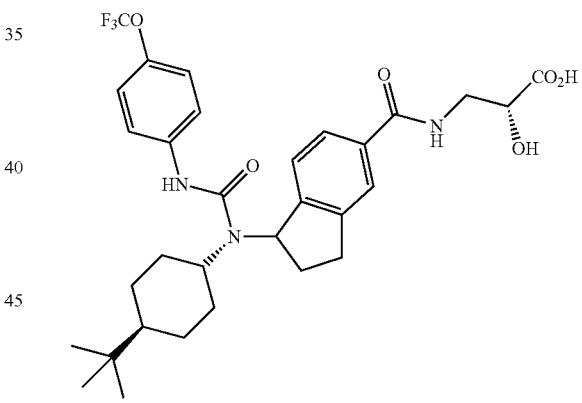

(2R)-3-[({1-[(trans-4-tert-butylcyclohexyl)({[4-(trifluoromethoxy)phenyl]amino}carbonyl)amino]-2,3-dihydro-1H-inden-5-yl}carbonyl)amino]-2-hydroxypropanoic acid Preparation was described in Example 3/4. Enantiomer A: HPLC/MS: m/z=606.3 (M+1), $R_t$=3.98 min. $^1$H NMR (DMSO-$d_6$): δ 12.02 (1H, s), 8.36 (1H, t, J=5.5 Hz), 8.25 (1H, s), 7.68 (1H, s), 7.63 (1H, d, J=8.0 Hz), 7.40 (2H, d, J=9.5 Hz), 7.16 (2H, d, J=9.0 Hz), 7.12 (1H, d, J=8.0 Hz), 5.05 (1H, br s), 4.17 (1H, dd, J=5.5 Hz, 7.5 Hz), 3.39 (2H, m), 3.05 (1H, m), 2.84 (1H, m), 2.32 (2H, m), 1.80 (6H, m), 1.15 (2H, m), 1.01 (1H, m), 0.86 (9H, s). Enantiomer B: HPLC/MS and $^1$H NMR (DMSO-$d_6$) are identical to those of enantiomer A.

Example 7/8

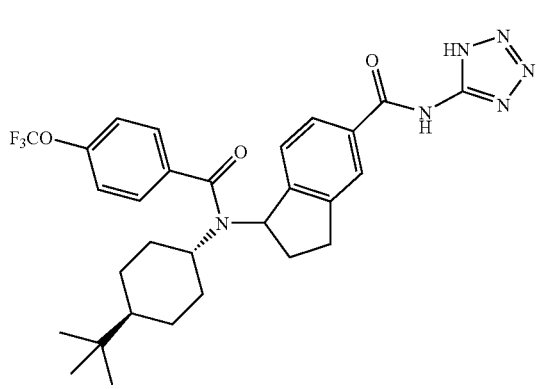

Step A. Butyl 1-{(trans-4-tert-butylcyclohexyl)[4-(trifluoromethoxy)benzoyl]amino}indane-5-carboxylate To a solution of butyl 1-[(trans-4-tert-butylcyclohexyl)amino]indane-5-carboxylate (0.30 g, 0.81 mmol) in anhydrous $CH_2Cl_2$ (10 mL) was added DIEA (0.29 mL, 1.62 mmol) and (4-trifluoromethoxy)benzoyl chloride (0.19 mL, 1.21 mmol). After stirring for 15 min at room temperature, the reaction mixture was poured into saturated $NaHCO_3$. The layers were separated and the aqueous layer was extracted once with $CH_2Cl_2$ (10 mL). The combined organic layers were dried over $Na_2SO_4$, filtered and concentrated. Chromatography (5% to 10% EtOAc in Hexane) gave butyl 1-{(trans-4-tert-butylcyclohexyl)[4-(trifluoromethoxy)benzoyl]amino} indane-5-carboxylate. HPLC/MS: m/z=560.3 (M+1), $R_t$=3.15 min. The racemic compound was then resolved on chiral HPLC (ChiralCel OD column, 5% EtOH in n-Heptane) to give enantiomer A (−) ($R_t$=6.07 min) and B (+) ($R_t$=8.33 min).

Step B. 1-{(trans-4-tert-butylcyclohexyl)[4-(trifluoromethoxy)benzoyl]amino}-N-1H-tetrazol-5-ylindane-5-carboxamide Butyl 1-{(trans-4-tert-butylcyclohexyl)[4-(trifluoromethoxy)benzoyl]amino}indane-5-carboxylate, enantiomer A (50 mg) or enantiomer B (70 mg), was saponified with aqueous LiOH and then coupled to 5-amino tetrazole following the procedure described (Step D., Example 1/2) to give 1-{(trans-4-tert-butylcyclohexyl)[4-(trifluoromethoxy)benzoyl]amino}-N-1H-tetrazol-5-ylindane-5-carboxamide. Enantiomer A: HPLC/MS: m/z=571.2 (M+1), $R_t$=2.65 min. $^1H$ NMR (DMSO-$d_6$): δ 12.34 (1H, br s), 7.95 (1H, s), 7.90 (1H, d, J=8.0 Hz), 7.52 (2H, d, J=8.0 Hz), 7.44 (2H, d, J=8.0 Hz), 7.35 (1H, d, J=8.0 Hz), 5.05 (1H, m), 3.35 (1H, m), 3.15 (1H, m), 2.96 (1H, m), 2.55 (1H, m), 2.36 (1H, m), 2.12 (1H, m), 1.77 (6H, m), 0.99 (1H, m), 0.84 (1H, m), 0.79 (9H, s). Enantiomer B: HPLC/MS and $^1H$ NMR (DMSO-$d_6$) are identical to those of enantiomer A.

Example 9/10

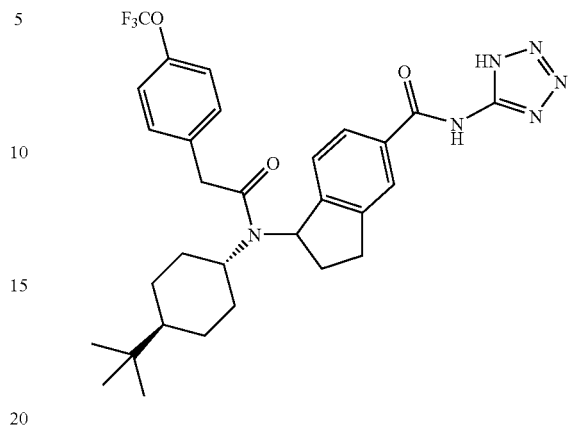

Step A. Butyl 1-((trans-4-tert-butylcyclohexyl){[4-(trifluoromethoxy)phenyl]acetyl}amino)indane-5-carboxylate To a solution of butyl 1-[(trans-4-tert-butylcyclohexyl)amino]indane-5-carboxylate (0.30 g, 0.81 mmol) in DMF/$CH_2CL_2$ (1:1, 10 mL) was added [4-(trifluoromethoxy)phenyl]acetic acid (0.21 g, 0.97 mmol), EDC (0.20 g, 1.05 mmol), HOBt (0.11 g, 0.81 mmol) and DIEA (0.45 mL, 2.43 mmol). After stirring at room temperature for 18 h, the reaction mixture was poured into saturated aqueous $NaHCO_3$ (20 mL) and extracted with EtOAc (30 mL). The organic layer was washed with brine (2×10 mL), dried over $Na_2SO_4$, filtered and concentrated. Chromatography (10% to 20% EtOAc in Hexane) gave 0.39 g (84% yield) of butyl 1-((trans-4-tert-butylcyclohexyl){[4-(trifluoromethoxy)phenyl]acetyl}amino)indane-5-carboxylate. HPLC/MS: m/z=574.2 (M+1), $R_t$=3.19 min. The racemic compound was then resolved on chiral HPLC (ChiralPak AD column, 5% EtOH in n-Heptane) to give enantiomer A (+) ($R_t$=8.65 min) and B (−) ($R_t$=12.0 min).

Step B. 1-((Trans-4-tert-butylcyclohexyl){[4-(trifluoromethoxy)phenyl]acetyl}amino)-N-1H-tetrazol-5-ylindane-5-carboxamide Butyl 1-((trans-4-tert-butylcyclohexyl){[4-(trifluoromethoxy)phenyl]acetyl}amino)indane-5-carboxylate, enantiomer A (55 mg) or enantiomer B (45 mg), was saponified with aqueous LiOH and then coupled to 5-amino tetrazole following the procedure described (Step D., Example 1/2) to give 1-((trans-4-tert-butylcyclohexyl){[4-(trifluoromethoxy)phenyl]acetyl}amino)-N-1H-tetrazol-5-ylindane-5-carboxamide. Enantiomer A: HPLC/MS: m/z=585.2 (M+1), $R_t$=2.75 min. $^1H$ NMR (DMSO-$d_6$): δ 12.30 (1H, br s), 7.90 (1H, s), 7.85 (1H, d, J=8.0 Hz), 7.31 (4H, s), 7.04 (1H, d, J=8.0 Hz), 4.83 (1H, m), 3.77 (2H, m), 3.37 (1H, m), 2.96 (1H, m), 3.08-3.00 (1H, m), 2.91-2.84 (1H, m), 2.41-2.31 (1H, m), 2.24-2.19 (1H, m), 1.78 (2H, m), 1.61 (2H, m), 1.18-0.95 (4H, m), 0.85 (9H, s). Enantiomer B: HPLC/MS and $^1H$ NMR (DMSO-$d_6$) are identical to those of enantiomer A.

Example 11

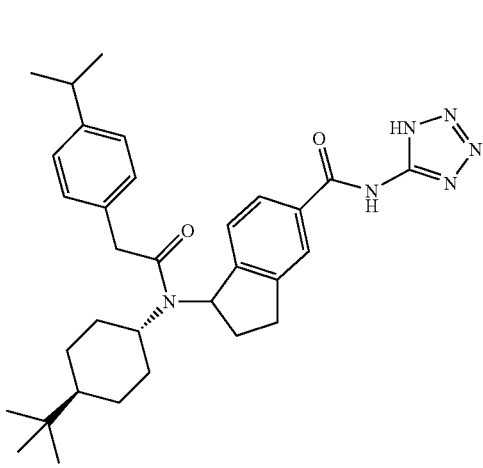

Step A. Butyl 1-{(trans-4-tert-butylcyclohexyl)][(4-isopropylphenyl)acetyl]amino}indane-5-carboxylate To a solution of enantiomer A of butyl 1-[(trans-4-tert-butylcyclohexyl)amino]indane-5-carboxylate, (41 mg, 0.11 mmol) in $CH_2CL_2$ (3 mL) was added (4-isopropylphenyl)acetic acid (98 mg, 0.55 mmol), EDC (105 mg, 0.55 mmol), HOBt (74 mg, 0.55 mmol) and DIEA (200 µL, 1.10 mmol). After stirring at room temperature for 18 h, the reaction mixture was poured into saturated aqueous $NaHCO_3$ (10 mL) and extracted with EtOAc (20 mL). The organic layer was washed with brine (2×10 mL), dried over $Na_2SO_4$, filtered and concentrated. Chromatography (10% EtOAc in Hexane) gave butyl 1-{(trans-4-tert-butylcyclohexyl)][(4-isopropylphenyl)acetyl]amino}indane-5-carboxylate. HPLC/MS: m/z=532.3 (M+1), $R_t$=3.15 min.

Step B. 1-{(Trans-4-tert-butylcyclohexyl)][(4-isopropylphenyl)acetyl]amino}-N-1H-tetrazol-5-ylindane-5-carboxamide Enantiomer A of butyl 1-{(trans-4-tert-butylcyclohexyl)[(4-isopropylphenyl)acetyl]amino}indane-5-carboxylate (36 mg) was saponified with aqueous LiOH and then coupled to 5-amino tetrazole following the procedure described (Step D., Example 1/2) to give 1-{(Trans-4-tert-butylcyclohexyl)[(4-isopropylphenyl)acetyl]amino}-N-1H-tetrazol-5-ylindane-5-carboxamide. HPLC/MS: m/z=543.5 (M+1), $R_t$=2.67 min. $^1$H NMR (DMSO-$d_6$): δ 12.30 (1H, br s), 7.90 (1H, s), 7.85 (1H, d, J=8.0 Hz), 7.17 (2H, d, J=8.0 Hz), 7.10 (2H, d, J=8.0 Hz), 7.03 (1H, d, J=8.0 Hz), 4.79 (1H, m), 3.74 (2H, m), 3.06 (1H, m), 2.88 (1H, m), 2.36 (1H, m), 2.21 (1H, m), 1.74 (2H, m), 1.54 (2H, m), 1.36-0.86 (13H, m), 0.84 (9H, s).

Following the procedures outlined for Examples 1-11 the compounds listed in Tables 1-7 were prepared

TABLE 1

| Example | Ar | R | LCMS data: retention time (min)/ M + H |
|---|---|---|---|
| 12 | 3,5-diClPh | 5-aminotetrazole amide | 4.36/570.2 |
| 13 | 3,5-diClPh | HN-CH2CH2-CO2H | 4.24/574.2 |
| 14 | 3,5-diClPh | HN-CH2-CH(OH)-CO2H | 4.14/590.2 |
| 15 | 3,5-diCF3Ph | 5-aminotetrazole amide | 2.83/638.3 |
| 16 | 3,5-diCF3Ph | HN-CH2CH2-CO2H | 4.33/642.2 |
| 17 | 3,5-diCF3Ph | HN-CH2-CH(OH)-CO2H | 4.22/658.2 |
| 18 | 6-methyl-2,2,4,4-tetrafluoro-benzodioxine | 5-aminotetrazole amide | 2.65/654.2 (M + Na+) |
| 19 | 6-methyl-2,2,4,4-tetrafluoro-benzodioxine | HN-CH2CH2-CO2H | 2.61/658.3 (M + Na+) |

TABLE 1-continued
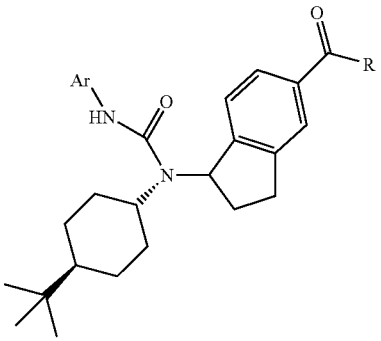
| Example | Ar | R | LCMS data: retention time (min)/ M + H |
|---|---|---|---|
| 20 | 4-iPrPh | 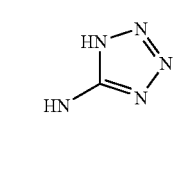 | 2.58/544.3 |
| 21 | 4-iPrPh | 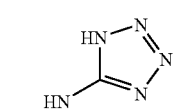 | 2.54/548.4 |
| 22 | 4-CHF₂O | 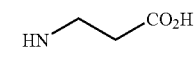 | 2.45/568.2 |
| 23 | 4-CHF₂O Ph | 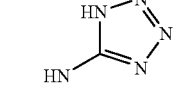 | 2.41/572.3 |
| 24 | 4-NMe₂Ph | 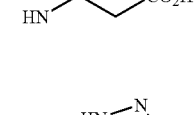 | 2.01/545.2 |
| 25 | 4-NMe₂Ph | 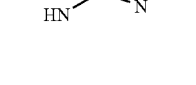 | 1.96/549.3 |
| 26 | 4-CF₃SPh |  | 2.64/602.2 |
| 27 | 4-CF₃SPh | 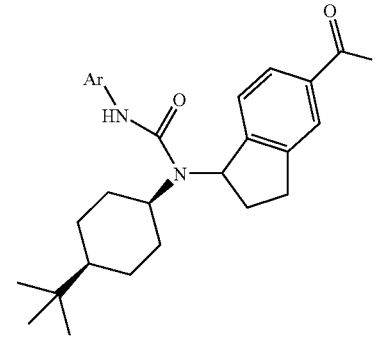 | 2.60/606.3 |
TABLE 2
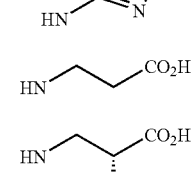
| Example | Ar | R | LCMS data: retention time (min)/ M + H |
|---|---|---|---|
| 28 | 4-CF₃OPh | 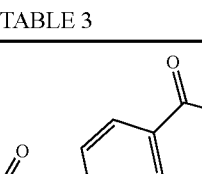 | 4.23/586.3 |
| 29 | 4-CF₃OPh | 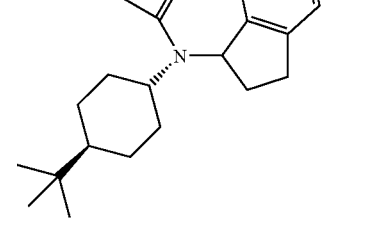 | 4.13/590.3 |
| 30 | 4-CF₃OPh | 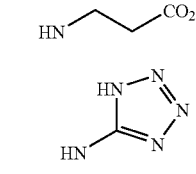 | 4.01/606.3 |
TABLE 3
| Example | Ar | R | LCMS data: retention time (min)/ M + H |
|---|---|---|---|
| 31 | 4-CF₃OPh | 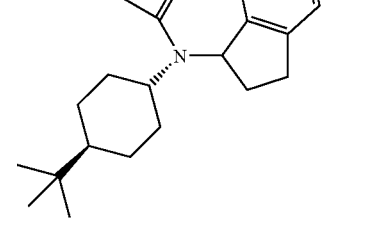 | 2.68/589.2 |
| 32 | 3,5-diMeOPh | 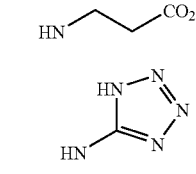 | 2.37/565.4 |
| 33 | 3,5-diMeOPh |  | 2.43/561.3 |

TABLE 3-continued

[Structure: Ar-CH2-C(=O)-N(cyclohexyl-4-tBu)-indanyl-C(=O)-R]

| Example | Ar | R | LCMS data: retention time (min)/M + H |
|---------|----|----|---|
| 34 | 4-EtOPh | HN-CH2CH2-CO2H | 2.45/549.4 |
| 35 | 4-EtOPh | HN-(5-tetrazolyl)-NH | 2.51/545.3 |
| 36 | 5-methyl-1,3-benzodioxol | HN-CH2CH2-CO2H | 2.34/549.4 |
| 37 | 5-methyl-1,3-benzodioxol | HN-(5-tetrazolyl)-NH | 2.40/545.4 |
| 38 | 4-MeOPh | HN-CH2CH2-CO2H | 2.37/535.4 |
| 39 | 4-MeOPh | HN-(5-tetrazolyl)-NH | 2.43/531.4 |
| 40 | 4-iPrPh | HN-CH2CH2-CO2H | 2.62/547.5 |
| 41 | 1-naphthyl | HN-(5-tetrazolyl)-NH | 2.54/551.3 |
| 42 | 1-naphthyl | HN-CH2CH2-CO2H | 2.49/555.4 |
| 43 | 4-BnOPh | HN-(5-tetrazolyl)-NH | 2.60/607.3 |
| 44 | 4-BnOPh | HN-CH2CH2-CO2H | 2.54/611.4 |
| 45 | 3-indolyl | HN-(5-tetrazolyl)-NH | 2.37/540.3 |
| 46 | 3-indolyl | HN-CH2CH2-CO2H | 2.31/544.4 |
| 47 | 3,4,5-triMeOPh | HN-(5-tetrazolyl)-NH | 2.34/591.3 |
| 48 | 3,4,5-triMeOPh | HN-CH2CH2-CO2H | 2.27/595.4 |
| 49 | 4-PentOPh | HN-(5-tetrazolyl)-NH | 2.72/587.3 |
| 50 | 4-PentOPh | HN-CH2CH2-CO2H | 2.68/591.5 |

TABLE 4

[Structure: Ar-NH-C(=O)-N(cyclohexyl-4-tBu)-tetrahydronaphthyl-C(=O)-R]

| Example | Ar | R | LCMS data: retention time (min)/M + H |
|---------|----|----|---|
| 51 | 4-CF3OPh | HN-(5-tetrazolyl)-NH | 4.23/600.3 |

TABLE 4-continued
| Example | Ar | R | LCMS data: retention time (min)/ M + H |
|---|---|---|---|
| 52 | 4-CF₃OPh | 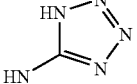 | 4.14/604.3 |
| 53 | 4-CF₃OPh | 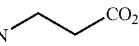 | 4.23/620.3 |
TABLE 5
| Example | Ar | R | LCMS data: retention time (min)/ M + H |
|---|---|---|---|
| 54 | 4-CF₃OPh | 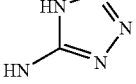 | 2.55/602.3 |
| 55 | 4-CF₃OPh | 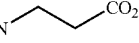 | 2.51/606.4 |
| 56 | 4-ᵗBuPh |  | 2.59/574.5 |
| 57 | 4-ᵗBuPh | 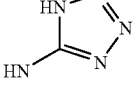 | 2.53/578.5 |
| 58 | 4-MeOPh |  | 2.32/548.5 |
| 59 | 4-MeOPh | 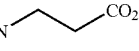 | 2.26/552.5 |
| 60 | 4-ⁿBuOPh | 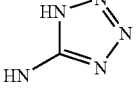 | 2.54/590.5 |
| 61 | 4-ⁿBuOPh | 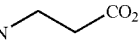 | 2.48/594.5 |
| 62 | 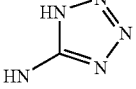 | 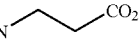 | 2.32/562.4 |
| 63 | 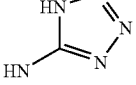 | 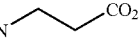 | 2.25/566.4 |
| 64 | 4-FPh | 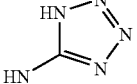 | 2.37/536.4 |
| 65 | 4-FPh |  | 2.31/540.4 |
| 66 | 4-ClPh | 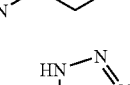 | 2.44/552.4 |
| 67 | 4-ClPh |  | 2.39/556.4 |
| 68 | 4-BrPh | | 2.47/596.3 |
| 69 | 4-BrPh | | 2.41/600.4 |

TABLE 5-continued
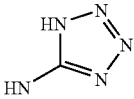
| Example | Ar | R | LCMS data: retention time (min)/ M + H |
|---|---|---|---|
| 70 | 2-CF₃OPh | 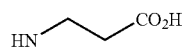 | 2.51/602.4 |
| 71 | 2-CF₃OPh | 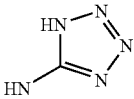 | 2.45/606.4 |
| 72 | 3-CF₃OPh | 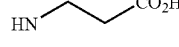 | 2.54/602.4 |
| 73 | 3-CF₃OPh | 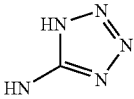 | 2.49/606.4 |
| 74 | 4-PhOPh | 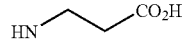 | 2.53/610.5 |
| 75 | 4-PhOPh | 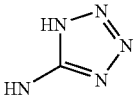 | 2.48 614.5 |
| 76 | 3,5-diClPh | 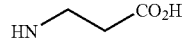 | 2.55/608.3 (M + Na⁺) |
| 77 | 3,5-diClPh | 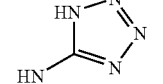 | 2.35/590.3 |
TABLE 6
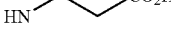
| Example | Ar | R | LCMS data: retention time (min)/ M + H |
|---|---|---|---|
| 78 | 3,5-diClPh | 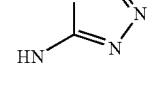 | 2.78/590.3 |
| 79 | 3,5-diClPh |  | 2.73/594.3 |
| 80 | 4-CF₃OPh |  | 2.71/606.4 |
| 81 | 4-CF₃OPh | | 2.66/610.4 |
TABLE 7
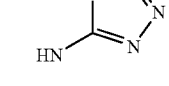
| Example | Ar | X | R | LCMS data: retention time (min)/ M + H |
|---|---|---|---|---|
| 82 | 3,5-diClPh | CH₂ |  | 2.82/604.2 |

TABLE 7-continued

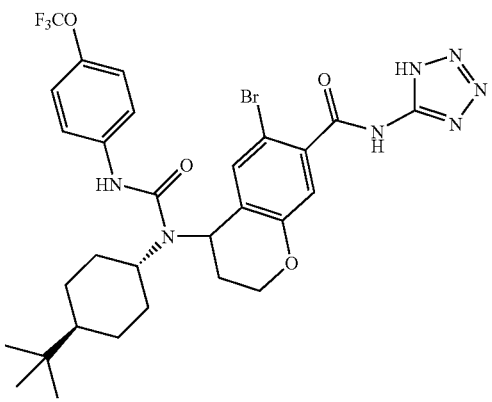

| Example | Ar | X | R | LCMS data: retention time (min)/ M + H |
|---|---|---|---|---|
| 83 | 3,5-diClPh | CH$_2$ | HN~CO$_2$H | 2.78/608.3 |
| 84 | 4-CF$_3$OPh | CH$_2$ | HN-tetrazole | 2.73/620.3 |
| 85 | 4-CF$_3$OPh | CH$_2$ | HN~CO$_2$H | 2.68/624.3 |
| 86 | 4-CF$_3$OPh | O | HN-tetrazole | 2.56/622.2 |
| 87 | 4-CF$_3$OPh | O | HN~CO$_2$H | 2.51/626.4 |

Example 88

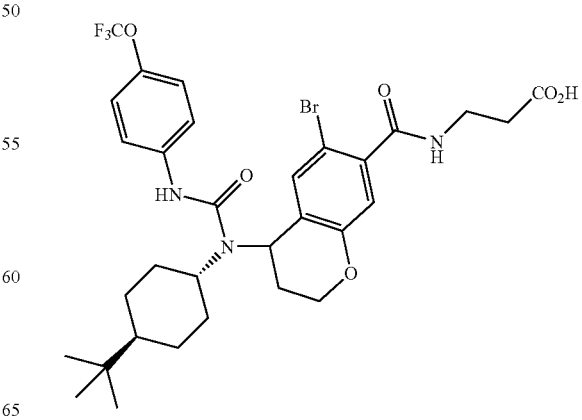

Step A. Methyl 6-bromo-4-oxochromane-7-carboxylate

Methyl 6-bromo-4-oxochromane-7-carboxylate was prepared by following literature procedure (*J. Org. Chem.* 1994, 59, 1216-1218). HPLC/MS: m/z=285.0 (M+1), R$_t$=1.87 min. $^1$H NMR (CDCl$_3$): δ 8.15 (1H, s), 7.38 (1H, s), 4.61 (2H, t, J=6.5 Hz), 3.98 (3H, s), 2.88 (2H, t, J=6.5 Hz).

Step B. Methyl 6-bromo-4-[(trans-4-tert-butylcyclohexyl)amino]chromane-7-carboxylate Methyl 6-bromo-4-[(trans-4-tert-butylcyclohexyl)amino] chromane-7-carboxylate was prepared following procedure described (Intermediate 4). HPLC/MS: nm/z=424.2 (M+1), R$_t$=1.95 min.

Step C. Methyl 6-bromo-4-[(trans-4-tert-butylcyclohexyl)({[4-(trifluoromethoxy)phenyl]amino}carbonyl)amino]chromane-7-carboxylate A solution of (4-trifluoromethoxy)phenyl isocyanate (0.35 mL, 2.30 mmol) and methyl 6-bromo-4-[(trans-4-tert-butylcyclohexyl)amino]chromane-7-carboxylate (0.49 g, 1.15 mmol) in dry THF (10 mL) was stirred for 1 h. Solvent evaporation and chromatography gave methyl 6-bromo-4-[(trans-4-tert-butylcyclohexyl)({[4-(trifluoromethoxy)phenyl]amino}carbonyl)amino]chromane-7-carboxylate. HPLC/MS: m/z=627.2 (M+1), R$_t$=2.82 min. $^1$H NMR (CDCl$_3$): δ 7.60 (1H, s), 7.41 (1H, s), 7.12 (4H, m), 6.01 (1H, br s), 4.88 (1H, br s), 4.48 (1H, dt, J=3.5 Hz, 10.5 Hz), 4.23 (1H, t, J=10.5 Hz), 3.97 (3H, s), 2.65 (1H, m), 2.14-1.93 (6H, m), 1.70-1.54 (2H, m), 1.27 (2H, m), 1.03 (1H, m), 0.91 (9H, s). The racemic compound was resolved on chiral HPLC (ChiralCel OD column, 10% EtOH in n-Hepatne) to give enantiomer A (+) (R$_t$=7.63 min) and B (−) (R$_t$=9.37 min).

Step D. 6-bromo-4-[(trans-4-tert-butylcyclohexyl)({[4-(trifluoromethoxy)phenyl]amino}carbonyl)amino]-N-1H-tetrazol-5-ylchromane-7-carboxamide Enantiomer A of methyl 6-bromo-4-[(trans-4-tert-butylcyclohexyl)({[4-(trifluoromethoxy)phenyl]amino}carbonyl)amino]chromane-7-carboxylate (25 mg) was saponified with aqueous LiOH and then coupled to 5-amino tetrazole following the procedure described (Step D., Example 1/2) to give 6-bromo-4-[(trans-4-tert-butylcyclohexyl)({[4-(trifluoromethoxy)phenyl]amino}carbonyl)amino]-N-1H-tetrazol-5-ylchromane-7-carboxamide. HPLC/MS: m/z=680.2 (M+1), R$_t$=2.55 min. $^1$H NMR (DMSO-d$_6$): δ 12.58 (1H, br s), 8.61 (1H, s), 7.47 (2H, dd, J=2.5 Hz, 8.5 Hz), 7.29 (1H, s), 7.21 (2H, d, J=8.5 Hz), 7.05 (1H, s), 4.71 (1H, m), 4.40 (1H, dt, J=2.5 Hz, 10.5 Hz), 4.25 (1H, t, J=10.5 Hz), 3.93 (1H, m), 2.77 (1H, m), 2.02 (1H, m), 1.90-1.67 (6H, m), 1.29-1.03 (4H, m), 0.88 (9H, s).

Example 89

N-({6-bromo-4-[(trans-4-tert-butylcyclohexyl)({[4-(trifluoromethoxy)phenyl]amino}carbonyl)amino]-3,4-dihydro-2H-chromen-7-yl}carbonyl)-β-alanine Enantiomer A of methyl 6-bromo-4-[(trans-4-tert-butylcyclohexyl)({[4-(trifluoromethoxy)phenyl]amino}carbonyl)amino]chromane-7-carboxylate (25 mg) was saponified with aqueous LiOH and then coupled to β-alanine methyl ester HCl salt following the procedure described (Example 3/4) to give N-({6-bromo-4-[(trans-4-tert-butylcyclohexyl)({[4-(trifluoromethoxy)phenyl]amino}carbonyl)amino]-3,4-dihydro-2H-chromen-7-yl}carbonyl)-β-alanine. HPLC/MS: m/z=684.2 (M+1), $R_t$=2.50 min. $^1$H NMR (DMSO-$d_6$): δ 12.20 (1H, br s), 8.56 (1H, s), 8.38 (1H, t, J=5.5 Hz), 7.46 (2H, d, J=9.0 Hz), 7.21 (2H, d, J=9.0 Hz), 6.72 (1H, s), 4.68 (1H, m), 4.36 (1H, dt, J=2.0 Hz, 11.5 Hz), 4.20 (1H, t, J=11.5 Hz), 3.90 (1H, m), 3.37 (2H, m), 2.73 (1H, m), 2.48 (2H, t, J=7.0 Hz), 1.98-1.72 (7H, m), 1.28-1.04 (4H, m), 0.88 (9H, s).

Biological Assays

The ability of the compounds of the present invention to inhibit the binding of glucagon and their utility in treating or preventing type 2 diabetes mellitus and the related conditions can be demonstrated by the following in vitro assays. Glucagon Receptor Binding Assay A stable CHO (Chinese hamster ovary) cell line expressing cloned human glucagon receptor was maintained as described (Chicchi et al. *J Biol Chem* 272, 7765-9 (1997); Cascieri et al. *J Biol Chem* 274, 8694-7 (1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/−compounds or 0.001 mM unlabeled glucagon. After 4-12 hours incubation at room temperature, the radioactivity bound to the cell membranes was determined in a radioactive emission detection counter (Wallac-Microbeta). Data was analyzed using the software program Prism° from GraphPad. The $IC_{50}$ values were calculated using non-linear regression analysis assuming single site competition. $IC_{50}$ values for the compounds of the invention are generally in the rangte of as low as about 1 nM to as high as about 500 nM, and thus have utility as glucagon antagonists.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{121}$I-labeled cAMP tracer (NEN). After 3 hours of incubation at room temperature the bound radioactivity was determined in a liquid scintillation counter (Top-Count-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

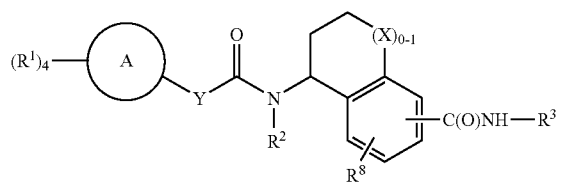

or a pharmaceutically acceptable salt thereof, wherein:

ring A is selected from the group consisting of: 6-10 membered aryl and 5-10 membered heteroaryl, said heteroaryl containing from 1-4 heteroatoms, 0-2 of which are O or S atoms, and 0-4 of which are N;

Y is present or absent, and when present, represents O, S, NH or $CH_2$;

X is present or absent, and when present, represents O or $CH_2$;

each $R^1$ is H or is selected from the group consisting of:
(a) halo, OH, $CO_2R^4$, $SO_pR^5$, CN, $NO_2$ $C(O)NR^6R^7$ or $NR^6R^7$;
(b) $C_{1-10}$alkyl, $C(O)C_{1-6}$alkyl or $OC_{1-6}$alkyl, the alkyl portions being optionally substituted with: (1) 1-5 halo groups, up to perhalo, and 1-2 groups selected from OH, $CO_2R^4$, $SO_pR^5$, CN, $NO_2$ $C(O)NR^6R^7$, $NR^6R^7$ and phenyl optionally substituted with 1-3 halo groups and 1-2 groups selected from: OH, $C_{1-3}$alkyl, halo$C_{1-3}$alkyl, CN, $OC_{1-3}$alkyl and Ohalo$C_{1-3}$alkyl;
(c) a 6-10 membered aryl or aryloxy group, said groups being optionally substituted with 1-3 halo groups and 1-2 groups selected from: OH, $C_{1-3}$alkyl, halo$C_{1-3}$alkyl, CN, $OC_{1-3}$alkyl and Ohalo$C_{1-3}$alkyl;

$R^2$ is $C_{1-10}$alkyl or aryl optionally substituted with 1-3 groups selected from (a), (b) and (c) above;

$R^3$ represents $CH_2CH_2CO_2R^4$, $CH_2CH(OH)CO_2R^4$, $CH_2CF_2CO_2R^4$ or 5-tetrazolyl;

$R^4$ is H or $C_{1-6}$alkyl, and $R^5$ represents a member selected from the group consisting of: $C_{1-10}$alkyl, Aryl or Ar—$C_{1-10}$alkyl, said $C_{1-10}$alkyl, Aryl and Ar—$C_{1-10}$alkyl being optionally substituted with 1-3 halo groups;

$R^6$ and $R^7$ each independently represent H or $C_{1-3}$alkyl, $R^8$ is selected from the group consisting of: H, OH, $C_{1-3}$alkyl, halo$C_{1-3}$alkyl, CN, $OC_{1-3}$alkyl and Ohalo$C_{1-3}$alkyl, and p is 0, 1 or 2.

2. A compound in accordance with claim 1 wherein ring A is selected from the group consisting of: phenyl, naphthyl, indole, 4H-1,3-benzodioxine and 1,3-benzodioxole.

3. A compound in accordance with claim 2 wherein ring A represents phenyl.

4. A compound in accordance with claim 1 wherein Y is absent or is selected from the group consisting of NH and $CH_2$.

5. A compound in accordance with claim 1 wherein X is absent or represents $CH_2$.

6. A compound in accordance with claim 1 wherein X is O.

7. A compound in accordance with claim 1 wherein $R^2$ represents $C_{1-10}$alkyl or phenyl optionally substituted with $C_{1-10}$alkyl or $OC_{1-6}$alkyl, said groups being optionally substituted with 1-5 halo groups up to perhalo.

8. A compound in accordance with claim 1 wherein $R^3$ represents $CH_2CH_2CO_2H$ or 5-tetrazolyl.

9. A compound in accordance with claim 1 wherein each $R^1$ is selected from the group consisting of: (a) H, halo, CN, $NR^6R^7$, with $R^6$ and $R^7$ representing H or $C_{1-6}$alkyl; (b) $C_{1-6}$alkyl, $OC_{1-6}$alkyl and $SC_{1-6}$alkyl, each optionally substituted with 1-5 halo groups; and (c) aryl optionally substituted with 1-4 halo groups or 1-2 members selected from $C_{1-6}$alkyl, $OC_{1-6}$alkyl, halo$C_{1-6}$alkyl and $OC_{1-6}$haloalkyl.

10. A compound in accordance with claim 1 wherein $R^8$ represents H, halo, $C_{1-3}$alkyl, halo$C_{1-3}$alkyl $OC_{1-3}$alkyl or Ohalo$C_{1-3}$alkyl.

11. A compound in accordance with claim 10 wherein $R^8$ represents H or halo.

12. A compound in accordance with claim 1 wherein:

A represents phenyl;

X is absent or represents $CH_2$;

Y is absent or is selected from the group consisting of; NH and $CH_2$;

each $R^1$ is selected from the group consisting of: (a) H, halo, CN, $NR^6R^7$, with $R^6$ and $R^7$ representing H or $C_{1-6}$alkyl; (b) $C_{1-6}$alkyl, $OC_{1-6}$alkyl and $SC_{1-6}$alkyl, each optionally substituted with 1-5 halo groups; and (c) aryl optionally substituted with 1-4 halo groups or 1-2 members selected from $C_{1-6}$alkyl, $OC_{1-6}$alkyl, halo$C_{1-6}$alkyl and $OC_{1-6}$haloalkyl;

$R^2$ represents $C_{1-10}$alkyl or phenyl optionally substituted with $C_{1-10}$alkyl or $OC_{1-6}$alkyl, said groups being optionally substituted with 1-5 halo groups up to perhalo;

$R^3$ represents $CH_2CH_2CO_2H$ or 5-tetrazolyl, and $R^8$ represents H or halo, and $R^8$ represents H or halo.

13. A compound in accordance with claim 1 wherein:

A represents phenyl;

X is O;

Y is absent or is selected from the group consisting of NH and $CH_2$;

each $R^1$ is selected from the group consisting of: (a) H, halo, CN, $NR^6R^7$, with $R^6$ and $R^7$ representing H or $C_{1-6}$alkyl; (b) $C_{1-6}$alkyl, $OC_{1-6}$alkyl and $SC_{1-6}$alkyl, each optionally substituted with 1-5 halo groups; and (c) aryl optionally substituted with 1-4 halo groups or 1-2 members selected from $C_{1-6}$alkyl, $OC_{1-6}$alkyl, halo$C_{1-6}$alkyl and $OC_{1-6}$haloalkyl;

$R^2$ represents $C_{1-10}$alkyl or phenyl optionally substituted with $C_{1-10}$alkyl or $OC_{1-6}$alkyl, said groups being optionally substituted with 1-5 halo groups up to perhalo;

$R^3$ represents $CH_2CH_2CO_2H$ or 5-tetrazolyl and $R^8$ represents H or halo, within this aspect of the invention, all other variables are as originally defined with respect to formula I.

14. A compound in accordance with claim 1 selected from one of the following tables:

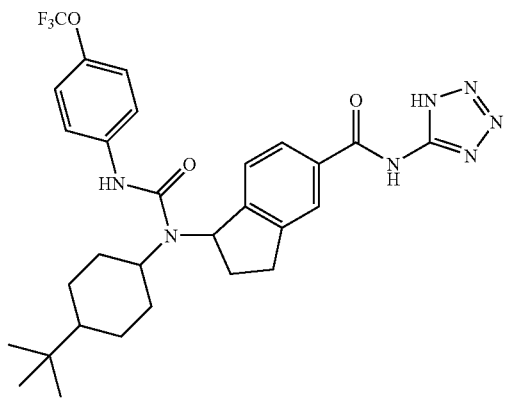

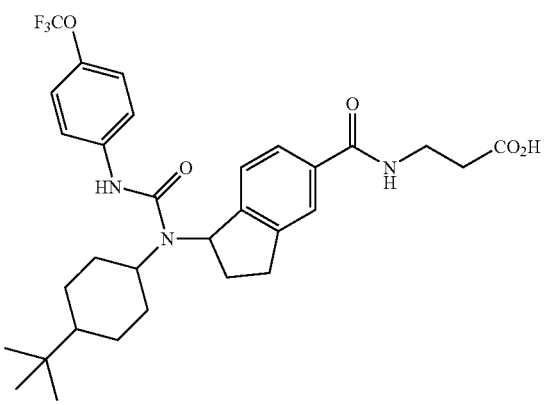

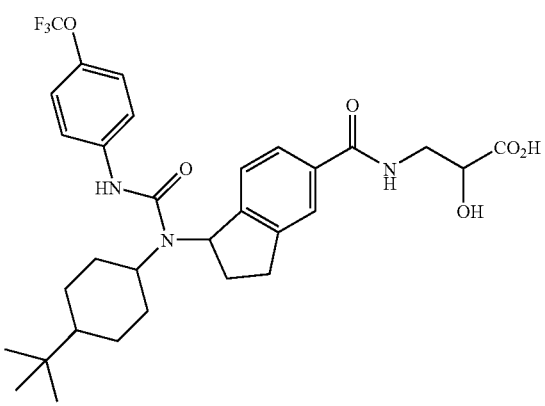

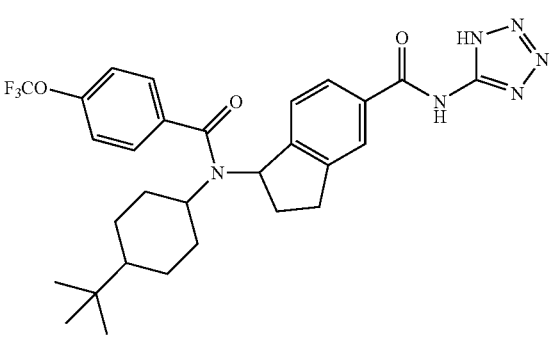

-continued
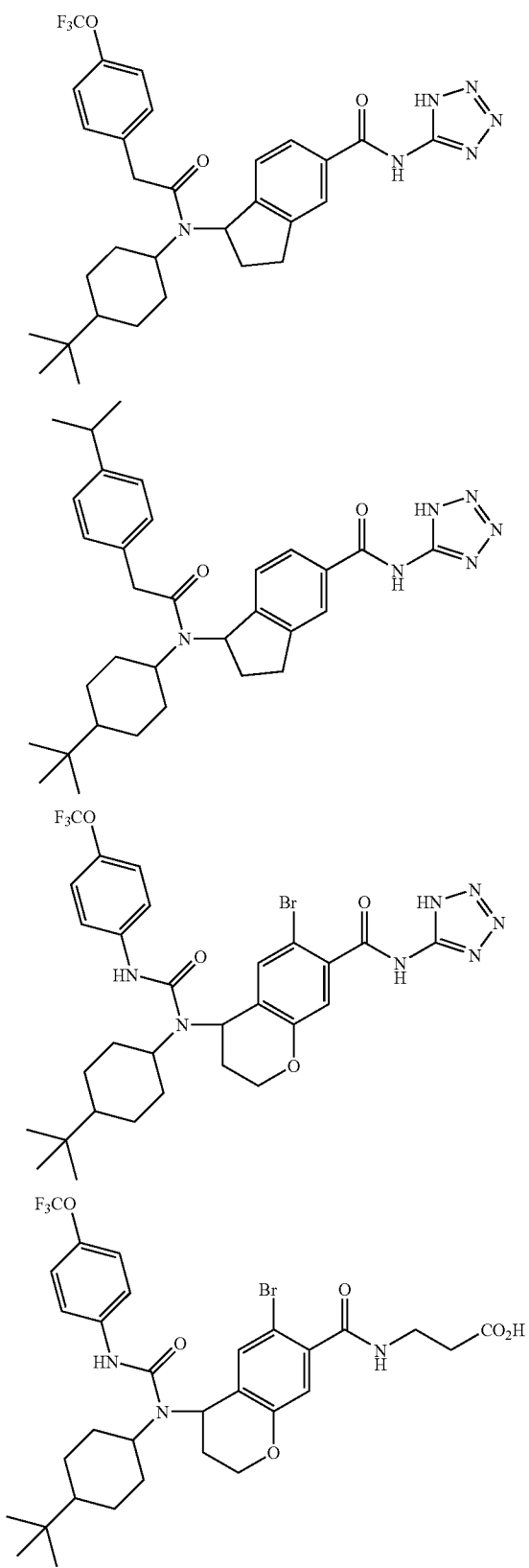
TABLE 1
| Example | Ar | R |
|---|---|---|
| 12 | 3,5-diClPh | 5-aminotetrazole |
| 13 | 3,5-diClPh | HN-CH2CH2-CO2H |
| 14 | 3,5-diClPh | HN-CH2-CH(OH)-CO2H |
| 15 | 3,5-diCF3Ph | 5-aminotetrazole |
| 16 | 3,5-diCF3Ph | HN-CH2CH2-CO2H |
| 17 | 3,5-diCF3Ph | HN-CH2-CH(OH)-CO2H |
| 18 | 4,4,2,2-tetrafluoro-6-methylbenzodioxine | 5-aminotetrazole |
| 19 | 4,4,2,2-tetrafluoro-6-methylbenzodioxine | HN-CH2CH2-CO2H |
| 20 | 4-iPrPh | 5-aminotetrazole |
| 21 | 4-iPrPh | HN-CH2CH2-CO2H |
| 22 | 4-CHF2O | 5-aminotetrazole |

TABLE 1-continued
| Example | Ar | R |
|---|---|---|
| 23 | 4-CHF$_2$O Ph | 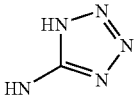 |
| 24 | 4-NMe$_2$Ph |  |
| 25 | 4-NMe$_2$Ph | 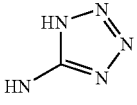 |
| 26 | 4-CF$_3$SPh |  |
| 27 | 4-CF$_3$SPh |  |
TABLE 2
| Example | Ar | R |
|---|---|---|
| 28 | 4-CF$_3$OPh | 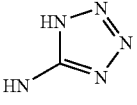 |
| 29 | 4-CF$_3$OPh |  |
| 30 | 4-CF$_3$OPh | 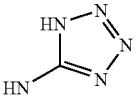 |
TABLE 3
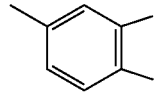
| Example | Ar | R |
|---|---|---|
| 31 | 4-CF$_3$OPh |  |
| 32 | 3,5-diMeOPh | 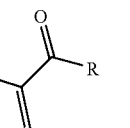 |
| 33 | 3,5-diMeOPh |  |
| 34 | 4-EtOPh |  |
| 35 | 4-EtOPh | 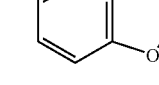 |
| 36 | 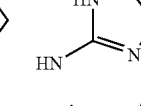 | |
| 37 |  | |
| 38 | 4-MeOPh | 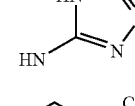 |
| 39 | 4-MeOPh |  |
| 40 | 4-$^i$Pr Ph | 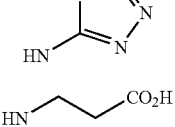 |
| 41 | 1-naphthyl | |
| 42 | 1-naphthyl |  |
| 43 | 4-BnOPh | 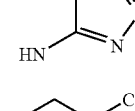 |
| 44 | 4-BnOPh |  |

TABLE 3-continued

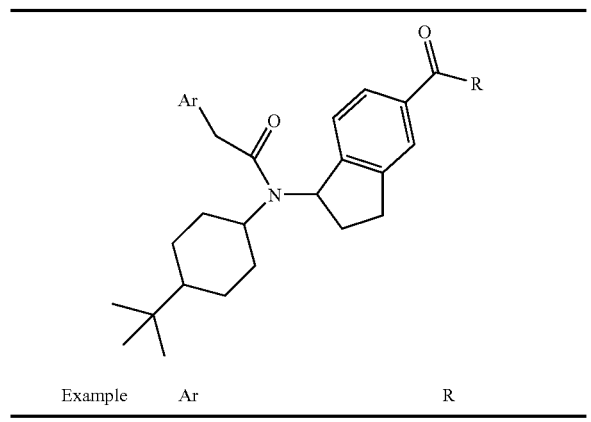

| Example | Ar | R |
|---|---|---|
| 45 | 3-indolyl | 5-aminotetrazole |
| 46 | 3-indolyl | HN-CH2CH2-CO2H |
| 47 | 3,4,5-triMeOPh | 5-aminotetrazole |
| 48 | 3,4,5-triMeOPh | HN-CH2CH2-CO2H |
| 49 | 4-PentOPh | 5-aminotetrazole |
| 50 | 4-PentOPh | HN-CH2CH2-CO2H |

TABLE 4

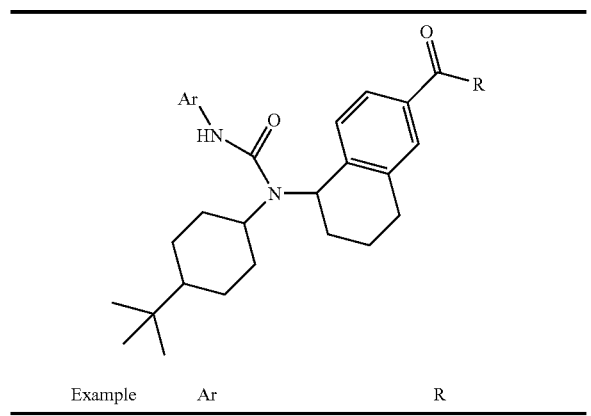

| Example | Ar | R |
|---|---|---|
| 51 | 4-CF3OPh | 5-aminotetrazole |
| 52 | 4-CF3OPh | HN-CH2CH2-CO2H |

TABLE 4-continued

| Example | Ar | R |
|---|---|---|
| 53 | 4-CF3OPh | HN-CH2-CH(OH)-CO2H |

TABLE 5

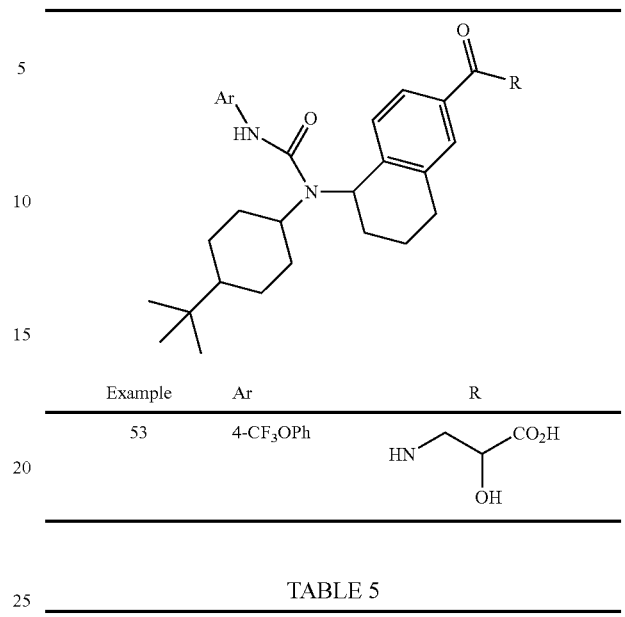

| Example | Ar | R |
|---|---|---|
| 54 | 4-CF3OPh | 5-aminotetrazole |
| 55 | 4-CF3OPh | HN-CH2CH2-CO2H |
| 56 | 4-tBuPh | 5-aminotetrazole |
| 57 | 4-tBuPh | HN-CH2CH2-CO2H |
| 58 | 4-MeOPh | 5-aminotetrazole |
| 59 | 4-MeOPh | HN-CH2CH2-CO2H |
| 60 | 4-nBuOPh | 5-aminotetrazole |

TABLE 5-continued

| Example | Ar | R |
|---|---|---|
| 61 | 4-"BuOPh | HN-CH2CH2-CO2H |
| 62 | 5-methylbenzo[1,3]dioxole | HN-tetrazole |
| 63 | 5-methylbenzo[1,3]dioxole | HN-CH2CH2-CO2H |
| 64 | 4-FPh | HN-tetrazole |
| 65 | 4-FPh | HN-CH2CH2-CO2H |
| 66 | 4-ClPh | HN-tetrazole |
| 67 | 4-ClPh | HN-CH2CH2-CO2H |
| 68 | 4-BrPh | HN-tetrazole |
| 69 | 4-BrPh | HN-CH2CH2-CO2H |
| 70 | 2-CF3OPh | HN-tetrazole |
| 71 | 2-CF3OPh | HN-CH2CH2-CO2H |
| 72 | 3-CF3OPh | HN-tetrazole |
| 73 | 3-CF3OPh | HN-CH2CH2-CO2H |

TABLE 5-continued

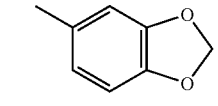

| Example | Ar | R |
|---|---|---|
| 74 | 4-PhOPh | HN-tetrazole |
| 75 | 4-PhOPh | HN-CH2CH2-CO2H |
| 76 | 3,5-diClPh | HN-tetrazole |
| 77 | 3,5-diClPh | HN-CH2CH2-CO2H |

TABLE 6

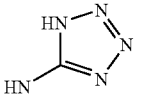

| Example | Ar | R |
|---|---|---|
| 78 | 3,5-diClPh | HN-tetrazole |
| 79 | 3,5-diClPh | HN-CH2CH2-CO2H |
| 80 | 4-CF3OPh | HN-tetrazole |
| 81 | 4-CF3OPh | HN-CH2CH2-CO2H |

TABLE 7

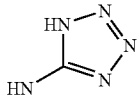

| Example | Ar | X | R |
|---------|-----|-----|-----|
| 82 | 3,5-diClPh | $CH_2$ | 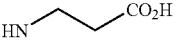 |
| 83 | 3,5-diClPh | $CH_2$ | 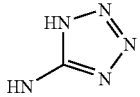 |
| 84 | 4-$CF_3$OPh | $CH_2$ | 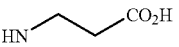 |
| 85 | 4-$CF_3$OPh | $CH_2$ | 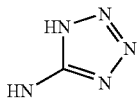 |
| 86 | 4-$CF_3$OPh | O | 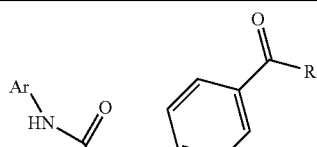 |

TABLE 7-continued

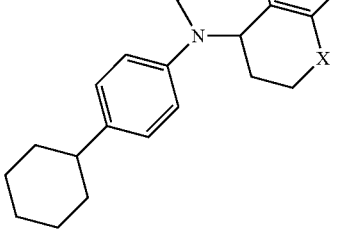

| Example | Ar | X | R |
|---------|-----|-----|-----|
| 87 | 4-$CF_3$OPh | O |  | or a pharmaceutically acceptable salt or solvate thereof.

15. A pharmaceutical composition comprising a compound in accordance with claim 1 in combination with a pharmaceutically acceptable carrier.

16. A method of treating type 2 diabetes mellitus in a mammalian patient in need of such treatment comprising administering to said patient a compound in accordance with claim 1 in an amount that is effective to treat said type 2 diabetes mellitus.

17. A method of delaying the onset of type 2 diabetes mellitus in a mammalian patient in need thereof, comprising administering to the patient a compound in accordance with claim 1 in an amount that is effective to delay the onset of said type 2 diabetes mellitus.

18. A method of treating hyperglycemia, diabetes or insulin resistance in a mammalian patient in need of such treatment which comprises administering to said patient an effective amount of a compound in accordance with claim 1.

19. A method of treating non-insulin dependent diabetes mellitus in a mammalian patient in need of such treatment comprising administering to the patient an anti-diabetic effective amount of a compound in accordance with claim 1.

\* \* \* \* \*